(12) United States Patent
Connors et al.

(10) Patent No.: US 7,304,207 B2
(45) Date of Patent: Dec. 4, 2007

(54) IDENTIFICATION AND CHARACTERIZATION OF AN ANTHOCYANIN MUTANT (ANT1) IN TOMATO

(75) Inventors: Karin A. Connors, Aloha, OR (US); Helena V. Mathews, Portland, OR (US); Xing Liang Liu, Tualatin, OR (US); Colby G. Caldwell, Oregon City, OR (US)

(73) Assignee: Exelixis, Inc., South San Francisco, CA (US)

( * ) Notice: Subject to any disclaimer, the term of this patent is extended or adjusted under 35 U.S.C. 154(b) by 500 days.

(21) Appl. No.: 10/407,845

(22) Filed: Apr. 4, 2003

(65) Prior Publication Data

US 2003/0226174 A1    Dec. 4, 2003

Related U.S. Application Data

(63) Continuation-in-part of application No. 10/033,190, filed on Oct. 29, 2001.

(60) Provisional application No. 60/369,998, filed on Apr. 4, 2002, provisional application No. 60/369,906, filed on Apr. 4, 2002.

(51) Int. Cl.
C12N 15/29 (2006.01)
C12N 15/63 (2006.01)
C12N 15/82 (2006.01)
A01H 5/00 (2006.01)

(52) U.S. Cl. ............... 800/282; 800/317.3; 800/317.4
(58) Field of Classification Search ............... 536/23.1, 536/23.6; 435/320.1, 419; 800/282, 298, 800/317.3, 317.4
See application file for complete search history.

(56) References Cited

U.S. PATENT DOCUMENTS

| | | | |
|---|---|---|---|
| 5,349,125 A | 9/1994 | Holton et al. | |
| 5,569,832 A | 10/1996 | Holton et al. | |
| 5,733,759 A | 3/1998 | Taylor et al. | |
| 5,831,060 A | 11/1998 | Wada et al. | |
| 5,859,329 A | 1/1999 | Holton et al. | |
| 5,861,487 A | 1/1999 | Holton et al. | |
| 6,054,636 A | 4/2000 | Fader | |
| 6,608,246 B1 | 8/2003 | Bovy et al. | |
| 7,034,138 B2 * | 4/2006 | Connors et al. | ........... 536/23.6 |
| 2003/0226174 A1 | 12/2003 | Connors et al. | |

OTHER PUBLICATIONS

. Fourgoux-Nicol et al 1999, Plant Molecular Biology 40: pp. 857-872.*
Broun P. et al. Science vol. 282; Nov. 13, 1998, pp. 1315-1317.*
de Pater S. et al. Plant Molecular Biology, 1997; vol. 34, 169-174.*
Liu C. et al. PNAS, 2002, vol. 99, No. 22; pp. 14578-14583.*
Quattrocchio F. et al. The Plant Cell; Aug. 1999, vol. 11, pp. 1433-1444.*
Quattrocchio et al., "Molecular Analysis of the anthocyanin2 Gene of Petunia and Its Role in the Evolution of Flower Color." The Plant Cell, vol. 11, 1433-1444, Aug. 1999.
Bovy et al., "High-Flavonol Tomatoes Resulting from the Heterologous Expression of the Maize Transcription Factor Genes LC and C1." The Plant Cell, vol. 14, 2509-2526, Oct. 2002.
Spelt et al., "ANTHOCYANIN1 of Petunia Controls Pigment Synthesis, Vacuolar pH, and Seed Coat Development by Genetically Distinct Mechanisms." The Plant Cell, vol. 14, 2121-2135, Sep. 2002.
Spelt et al., "Anthocyanin1 of Petunia Encodes a Basic Helix-Loop-Helix Protein that Directly Activates Transcription of Structural Anthocyanin Genes." The Plant Cell, vol. 12, 1619-1631, Sep. 2000.
Connors et al., "Identification and Characterization of an Anthocyanin Mutant (ANT1) in Tomato." U.S. Appl. No. 10/033,190, filed Oct. 29, 2001.
Alfenito et al., "Functional complementation of anthocyanin sequestration in the vacuole of widely divergent glutathione S-transferases," The Plant Cell, 10:1135-1149, 1998.
Bowie et al., "Deciphering the Message in Protein Sequences: Tolerance to Amino Acid Substitutions," Science, 247(4948):1306-1310, 1990.
Broun et al., "Catalytic Plasticity of Fatty Acid Modification Enzymes Underlying Chemical Diversity of Plant Lipids," Science, 282(5392):1315-1317, 1998.
Cone et al., "Clonded Anthocyanin Genes and Their Regulation," The Maize Handbook, Freeling et al., Springer-Verlag, New York, pp. 282-285, 1994.
Debeaujon et al., "The Transparent TESTA12 Gene of Arabidopsis Encodes a Multidrug Secondary Transporter-like Protein Required for Flavonoid Sequestration in Vacuoles of the Seed Coat Endothelium," The Plant Cell, 13:853-871, 2001.
De Pater et al., "RAP-1 is an Arabidopsis MYC-like R protein homologue, that binds to G-box sequence motifs," Plant Molecular Biology, 34(1):169-174, 1997.
Dong, X., "Functional Conservation of Plant Secondary Metabolic Enzymes Revealed by Complementation of Arabidopsis flavonoid Mutants with Maize Genes," Plant Physiology, 127:46-57, 2001.
Fourgoux-Nicol et al., "Isolation of rapeseed genes expressed early and specifically during development of the male gametophyte," Plant Molecular Biology, 40(5):857-872, 1999.
Islam, M., "Anthocyanin Compositions in Sweetpotato (Ipomoea batatas L.) Leaves," Biosci. Biotechnol. Biochem., 66(11):2483-2486, 2002.

(Continued)

Primary Examiner—Russell P. Kallis
(74) Attorney, Agent, or Firm—Klarquist Sparkman, LLP

(57) ABSTRACT

The present invention is directed to a novel plant phenotype, designated Anthocyanin 1 (ANT1), a nucleic acid sequence expressed in plants demonstrating the ANT1 phenotype and the corresponding amino acid sequence. Also provided are plant cells and plants that exhibit modified ANT1 expression.

11 Claims, 1 Drawing Sheet

OTHER PUBLICATIONS

Liu et al., "Bottlenecks for metabolic engineering of isoflavone glycoconjugates in *Arabidopsis*," *PNAS*, 99(22):14578-14583, 2002.

McConnell et al., "Role of *PHABULOSA* and *PHAVOLUTA* in determining radial patterning in shoots," *Nature*, 411(6838):709-713, 2001.

Proteggente et al., "The antioxidant activity of regularly consumed fruit and vegetables reflects their phenolic and vitamin C composition," *Free Radicals Research*, 36(2):217-233, 2002.

Verpoorte and Memelink, "Engineering secondary metabolite production plants," *Current Opinion in Biotechnology*, 13(2):181-187, 2002.

* cited by examiner

Cyanidin-3-glucoside

Cyanidin-3-rutinoside

SEQUENCE LISTING

<160> NUMBER OF SEQ ID NOS: 4

<210> SEQ ID NO 1
<211> LENGTH: 825
<212> TYPE: DNA
<213> ORGANISM: Lycopersicon esculentum

<400> SEQUENCE: 1

```
atgaacagta catctatgtc ttcattggga gtgagaaaag gttcatggac tgatgaagaa      60
gattttcttc taagaaaatg tattgataag tatggtgaag gaaaatggca tcttgttccc     120
ataagagctg gtctgaatag atgtcggaaa agttgtagat tgaggtggct gaattatcta     180
aggccacata tcaagagagg tgactttgaa caagatgaag tggatctcat tttgaggctt     240
cataagctct taggcaacag atggtcactt attgctggta gacttcccgg aaggacagct     300
aacgatgtga aaactattg gaacactaat cttctaagga agttaaatac tactaaaatt     360
gttcctcgcg aaaagattaa caataagtgt ggagaaatta gtactaagat tgaaattata     420
aaacctcaac gacgcaagta tttctcaagc acaatgaaga atgttacaaa caataatgta     480
attttggacg aggaggaaca ttgcaaggaa ataataagtg agaaacaaac tccagatgca     540
tcgatggaca acgtagatcc atggtggata aatttactgg aaaattgcaa tgacgatatt     600
gaagaagatg aagaggttgt aattaattat gaaaaaacac taacaagttt gttacatgaa     660
gaaatatcac caccattaaa tattggtgaa ggtaactcca tgcaacaagg acaaataagt     720
catgaaaatt ggggtgaatt ttctcttaat ttaccaccca tgcaacaagg agtacaaaat     780
gatgattttt ctgctgaaat tgacttatgg aatctacttg attaa                     825
```

<210> SEQ ID NO 2
<211> LENGTH: 274
<212> TYPE: PRT
<213> ORGANISM: Lycopersicon esculentum

<400> SEQUENCE: 2

```
Met Asn Ser Thr Ser Met Ser Ser Leu Gly Val Arg Lys Gly Ser Trp
1               5                   10                  15

Thr Asp Glu Glu Asp Phe Leu Leu Arg Lys Cys Ile Asp Lys Tyr Gly
                20                  25                  30

Glu Gly Lys Trp His Leu Val Pro Ile Arg Ala Gly Leu Asn Arg Cys
            35                  40                  45

Arg Lys Ser Cys Arg Leu Arg Trp Leu Asn Tyr Leu Arg Pro His Ile
        50                  55                  60

Lys Arg Gly Asp Phe Glu Gln Asp Glu Val Asp Leu Ile Leu Arg Leu
65                  70                  75                  80

His Lys Leu Leu Gly Asn Arg Trp Ser Leu Ile Ala Gly Arg Leu Pro
                85                  90                  95

Gly Arg Thr Ala Asn Asp Val Lys Asn Tyr Trp Asn Thr Asn Leu Leu
            100                 105                 110

Arg Lys Leu Asn Thr Thr Lys Ile Val Pro Arg Glu Lys Ile Asn Asn
        115                 120                 125

Lys Cys Gly Glu Ile Ser Thr Lys Ile Glu Ile Lys Pro Gln Arg
    130                 135                 140

Arg Lys Tyr Phe Ser Ser Thr Met Lys Asn Val Thr Asn Asn Val
145                 150                 155                 160

Ile Leu Asp Glu Glu Glu His Cys Lys Glu Ile Ile Ser Glu Lys Gln
```

```
                165              170              175
Thr Pro Asp Ala Ser Met Asp Asn Val Asp Pro Trp Trp Ile Asn Leu
            180              185              190

Leu Glu Asn Cys Asn Asp Asp Ile Glu Glu Asp Glu Glu Val Val Ile
            195              200              205

Asn Tyr Glu Lys Thr Leu Thr Ser Leu Leu His Glu Glu Ile Ser Pro
            210              215              220

Pro Leu Asn Ile Gly Glu Gly Asn Ser Met Gln Gln Gly Gln Ile Ser
225              230              235              240

His Glu Asn Trp Gly Glu Phe Ser Leu Asn Leu Pro Pro Met Gln Gln
            245              250              255

Gly Val Gln Asn Asp Asp Phe Ser Ala Glu Ile Asp Leu Trp Asn Leu
            260              265              270

Leu Asp

<210> SEQ ID NO 3
<211> LENGTH: 1012
<212> TYPE: DNA
<213> ORGANISM: Lycopersicon esculentum

<400> SEQUENCE: 3
atgaacagta catctatgtc ttcattggga gtgagaaaag gttcatggac tgatgaagaa      60
gattttcttc taagaaaatg tattgataag tatggtgaag gaaaatggca tcttgttccc     120
ataagagctg gtaactatta aattaactat cacgttattt ttatttgtct ttctgtctca     180
ttttatttga cgttattacg aatatcatct gaaaatgtac gtgcaggtct gaatagatgt     240
cggaaaagtt gtagattgag gtggctgaat tatctaaggc cacatatcaa gagaggtgac     300
tttgaacaag atgaagtgga tctcattttg aggcttcata agctcttagg caacaggcat     360
gcaagtttat gttttgacaa aatttgatta gtatatatta tatacgtgt gactatttc      420
atctaaatgt tacgttattt tacgtagatg gtcacttatt gctggtagac ttcccggaag     480
gacagctaac gatgtgaaaa actattggaa cactaatctt ctaaggaagt taaatactac     540
taaaattgtt cctcgcgaaa agattaacaa taagtgtgga gaaattagta ctaagattga     600
aattataaaa cctcaacgac gcaagtattt ctcaagcaca atgaagaatg ttacaaacaa     660
taatgtaatt ttggacgagg aggaacattg caaggaaata ataagtgaga aacaaactcc     720
agatgcatcg atgacaacg tagatccatg gtggataaat ttactggaaa attgcaatga     780
cgatattgaa gaagatgaag aggttgtaat taattatgaa aaaacactaa caagtttgtt     840
acatgaagaa atatcaccac cattaaatat tggtgaaggt aactccatgc aacaaggaca     900
aataagtcat gaaaattggg gtgaattttc tcttaattta ccacccatgc aacaggagt      960
acaaaatgat gattttctg ctgaaattga cttatggaat ctacttgatt aa            1012

<210> SEQ ID NO 4
<211> LENGTH: 12241
<212> TYPE: DNA
<213> ORGANISM: Artificial
<220> FEATURE:
<223> OTHER INFORMATION: Oligonucleotide

<400> SEQUENCE: 4
tgagcgtcgc aaaggcgctc ggtcttgcct tgctcgtcgg tgatgtactt caccagctcc      60
gcgaagtcgc tcttcttgat ggagcgcatg gggacgtgct tggcaatcac gcgcacccc     120
```

-continued

```
cggccgtttt agcggctaaa aaagtcatgg ctctgccctc gggcggacca cgcccatcat    180
gaccttgcca agctcgtcct gcttctcttc gatcttcgcc agcagggcga ggatcgtggc    240
atcaccgaac cgcgccgtgc gcgggtcgtc ggtgagccag agtttcagca ggccgcccag    300
gcggcccagg tcgccattga tgcgggccag ctcgcggacg tgctcatagt ccacgacgcc    360
cgtgattttg tagccctggc cgacggccag caggtaggcc gacaggctca tgccggccgc    420
cgccgccttt tcctcaatcg ctcttcgttc gtctggaagg cagtacacct tgataggtgg    480
gctgcccttc ctggttggct tggtttcatc agccatccgc ttgccctcat ctgttacgcc    540
ggcggtagcc ggccagcctc gcagagcagg attcccgttg agcaccgcca ggtgcgaata    600
agggacagtg aagaaggaac acccgctcgc gggtgggcct acttcaccta tcctgcccgg    660
ctgacgccgt tggatacacc aaggaaagtc tacacgaacc ctttggcaaa atcctgtata    720
tcgtgcgaaa aaggatggat ataccgaaaa atcgctata atgaccccga agcagggtta     780
tgcagcggaa aagcgccacg cttcccgaag ggagaaaggc ggacaggtat ccggtaagcg    840
gcagggtcgg aacaggagag cgcacgaggg agcttccagg gggaaacgcc tggtatcttt    900
atagtcctgt cgggtttcgc cacctctgac ttgagcgtcg attttttgtga tgctcgtcag    960 gggggcggag cctatggaaa aacgccagca acgcggcctt tttacggttc ctggccttt    1020 gctgcctttt tgctcacatg ttctttcctg cgttatcccc tgattctgtg ataaccgta    1080 ttaccgcctt tgagtgagct gataccgctc gccgcagccg aacgaccgag cgcagcgagt    1140
cagtgagcga ggaagcggaa gagcgccaga aggccgccag agaggccgag cgcggccgtg    1200
aggcttggac gctagggcag ggcatgaaaa agcccgtagc gggctgctac gggcgtctga    1260
cgcggtggaa aggggagg gatgttgtct acatggctct gctgtagtga gtgggttgcg    1320
ctccggcagc ggtcctgatc aatcgtcacc cttctcggt ccttcaacgt tcctgacaac   1380
gagcctcctt ttcgccaatc catcgacaat caccgcgagt ccctgctcga acgctgcgtc    1440
cggaccggct tcgtcgaagg cgtctatcgc ggcccgcaac agcggcgaga gcggagcctg    1500
ttcaacggtg ccgccgcgct cgccggcatc gctgtcgccg gcctgctcct caagcacggc    1560
cccaacagtg aagtagctga ttgtcatcag cgcattgacg gcgtccccgg ccgaaaaacc    1620
cgcctcgcag aggaagcgaa gctgcgcgtc ggccgttttcc atctgcggtg cgcccggtcg    1680
cgtgccggca tggatgcgcg cgccatcgcg gtaggcgagc agcgcctgcc tgaagctgcg    1740
ggcattcccg atcagaaatg agcgccagtc gtcgtcggct ctcggcaccg aatgcgtatg    1800
attctccgcc agcatggctt cggccagtgc gtcgagcagc gcccgcttgt tcctgaagtg    1860
ccagtaaagc gccggctgct gaaccccaa ccgttccgcc agtttgcgtg tcgtcagacc    1920
gtctacgccg acctcgttca acaggtccag ggcggcacgg atcactgtat tcggctgcaa    1980 cttttgtcatg cttgacactt tatcactgat aaacataata tgtccaccaa cttatcagtg    2040
ataaagaatc cgcgcgttca atcggaccag cggaggctgg tccggaggcc agacgtgaaa    2100
cccaacatac ccctgatcgt aattctgagc actgtcgcgc tcgacgctgt cggcatcggc    2160
ctgattatgc cggtgctgcc gggcctcctg cgcgatctgg ttcactcgaa cgacgtcacc    2220
gcccactatg gcattctgct ggcgctgtat gcgttggtgc aatttgcctg cgcacctgtg    2280
ctgggcgcgc tgtcggatcg tttcgggcgg cggccaatct tgctcgtctc gctggccggc    2340
gccagatctg gggaaccctg tggttggcat gcacatacaa atggacgaac ggataaacct    2400
tttcacgccc ttttaaatat ccgattattc taataaacgc tcttttctct taggtttacc    2460
cgccaatata tcctgtcaaa cactgatagt ttaaactgaa ggcgggaaac gacaatctga    2520
```

-continued

```
tcatgagcgg agaattaagg gagtcacgtt atgaccccg ccgatgacgc gggacaagcc      2580
gttttacgtt tggaactgac agaaccgcaa cgttgaagga gccactcagc cgatctgaat      2640
tcccgatcta gtaacataga tgacaccgcg cgcgataatt tatcctagtt tgcgcgctat      2700
attttgtttt ctatcgcgta ttaaatgtat aattgcggga ctctaatcat aaaaacccat      2760
ctcataaata acgtcatgca ttacatgtta attattacat gcttaacgta attcaacaga      2820
aattatatga taatcatcgc aagaccggca acaggattca atcttaagaa actttattgc      2880
caaatgtttg aacgatcggg gaaattcgcg agctcggtac ccgctctaga actagtggat      2940
cccccgggct gcaggaattc aaacttacaa atttctctga acttgtatcc tcagtacttc      3000
aaagaaaata gcttacacca aatttttct tgttttcaca aatgccgaac ttggttcctt      3060 ataggaaa actcaagggc aaaaatgaca cggaaaaata taaaggata agtagtgggg      3120 gataagattc ctttgtgata aggttacttt ccgcccttac attttccacc ttacatgtgt      3180
cctctatgtc tctttcacaa tcaccgacct tatcttcttc ttttcattgt tgtcgtcagt      3240
gcttacgtct tcaagattct tttcttcgcc tggttcttct ttttcaattt ctacgtattc      3300
ttcttcgtat tctggcagta taggatcttg tatctgtaca ttcttcattt ttgaacatag      3360
gttgcatatg tgccgcatat tgatctgctt cttgctgagc tcacataata cttccatagt      3420
ttttcccgta aacattggat tcttgatgct acatcttgga taattacctt ctcgtaccaa      3480
gcttaattga gatgattagc ccagacccag caggattagg cttaatggtg gtccatttga      3540
gaaaaagatt aaaaatgatg tcataaaaaa acgtggtcgg caggattcga acctgcgcgg      3600
gcaaagccca catgatttct agtcatgccc gataaccact ccggcacgac cacaatgatg      3660
ctacaattgc tttgttgtaa tcattaactt atggttgagt ttgatgctga ttaatactat      3720
tatgtttcca ttaactactt ttgaagtata caaaattacg aatttataac caaatttgag      3780
gtataatatg cgagagctac ctaaattttt cttacttaat tttaaagtac attcaaattc      3840
tgaatttata ttgtgtatag tcagaaaaca atctacatat ttaaacacat aaatttctca      3900
cgtttataat caattttgtc ggttcctgta attttctaa aataaaagc aaccaaaatt      3960 gtgcatcaac ttattacata ccatgggaaa tgcaaacttc aaacttatg gactcaaagg      4020 gtacatatct aaactacata ttgtcagatt cttcactctt atttcttgag ggcctcgagg      4080
cattaccaac caaatccaaa aattgctttc gaatctcaat aaaaaggata accccatgaa      4140
aaagacgtgg acggcaggat tcgaacctgc gcgcagagcc cacatgattt ctagtcatgc      4200
ccgataacca ctccggcacg tccacttcac tgttaacgtt tacagtaaca agtcactaac      4260
tactaatcaa cattagctca ggaaatcaaa actagattat ttacatttac aacgacatgt      4320
cgttcgaagt agttggtctg tatctgagta gctttggcgg gtagattcaa tcgcatttct      4380
gcatataaaa ctgatcctcc ctctatcgcc aaagtcaaac tgaaaagggc cgggggcaag      4440
atatgggagc ttggattgaa caagatggat tgcacgcagg ttctccggcc gcttgggtgg      4500
agaggctatt cggctatgac tgggcacaac agacaatcgg ctgctctgat gccgccgtgt      4560
tccggctgtc agcgcagggg cgcccggttc ttttttgtcaa gaccgacctg tccggtgccc      4620
tgaatgaact gcaggacgag gcagcgcggc tatcgtggct ggccacgacg ggcgttcctt      4680
gcgcagctgt gctcgacgtt gtcactgaag cgggaaggga ctggctgcta ttgggcgaag      4740
tgccggggca ggatctcctg tcatctcacc ttgctcctgc cgagaaagta tccatcatgg      4800
ctgatgcaat gcggcggctg catacgcttg atccggctac ctgcccattc gaccaccaag      4860
```

```
cgaaacatcg catcgagcga gcacgtactc ggatggaagc cggtcttgtc gatcaggatg   4920
atctggacga agagcatcag gggctcgcgc cagccgaact gttcgccagg ctcaaggcgc   4980
gcatgcccga cggcgaggat ctcgtcgtga cccatggcga tgcctgcttg ccgaatatca   5040
tggtggaaaa tggccgcttt tctggattca tcgactgtgg ccggctgggt gtggcggacc   5100
gctatcagga catagcgttg ctacccgtg  atattgctga agagcttggc ggcgaatggg   5160
ctgaccgctt cctcgtgctt tacggtatcg ccgctcccga ttcgcagcgc atcgccttct   5220
atcgccttct tgacgagttc ttctgacgat gagctaagct agctatatca tcaatttatg   5280
tattacacat aatatcgcac tcagtctttc atctacggca atgtaccagc tgatataatc   5340
agttattgaa atatttctga atttaaactt gcatcaataa atttatgttt ttgcttggac   5400
tataatacct gacttgttat tttatcaata aatatttaaa ctatatttct ttcaagatgg   5460
gaattaattc actggccgtc gttttacaac gtcgtgactg ggaaaaccct ggcgttaccc   5520
aacttaatcg ccttgcagca catccccctt tcgccagctg gcgtaatagc gaagaggccc   5580
gcaccgatcg cccttcccaa cagttgcgca gcctgaatgg cgcccgctcc tttcgctttc   5640
ttcccttcct ttctcgccac gttcgccggc tttccccgtc aagctctaaa tcggggctc   5700 cctttagggt tccgatttag tgctttacgg cacctcgacc ccaaaaaact tgatttgggt   5760
gatggttcac gtagtgggcc atcgccctga tagacggttt ttcgcccttt gacgttggag   5820
tccacgttct ttaatagtgg actcttgttc caaactggaa caacactcaa ccctatctcg   5880
ggctattctt ttgatttata agggattttg ccgatttcgg aaccaccatc aaacaggatt   5940
ttcgcctgct ggggcaaacc agcgtggacc gcttgctgca actctctcag ggccaggcgg   6000
tgaagggcaa tcagctgttg cccgtctcac tggtgaaaag aaaaaccacc ccagtacatt   6060
aaaaacgtcc gcaatgtgtt attaagttgt ctaagcgtca atttgtttac accacaatat   6120
atcctgccac cagccagcca acagctcccc gaccggcagc tcggcacaaa atcaccactc   6180
gatacaggca gcccatcagt ccgggacggc gtcagcggga gagccgttgt aaggcggcag   6240
actttgctca tgttaccgat gctattcgga agaacggcaa ctaagctgcc gggtttgaaa   6300
cacggatgat ctcgcggagg gtagcatgtt gattgtaacg atgacagagc gttgctgcct   6360
gtgatcaaat atcatctccc tcgcagagat ccgaattatc agccttctta ttcatttctc   6420
gcttaaccgt gacaggctgt cgatcttgag aactatgccg acataatagg aaatcgctgg   6480
ataaagccgc tgaggaagct gagtggcgct atttctttag aagtgaacgt tgacgatatc   6540 aactcccta tccattgctc accgaatggt acaggtcggg gacccgaagt tccgactgtc    6600
ggcctgatgc atccccggct gatcgacccc agatctgggg ctgagaaagc ccagtaagga   6660
aacaactgta ggttcgagtc gcgagatccc ccggaaccaa aggaagtagg ttaaacccgc   6720
tccgatcagg ccgagccacg ccaggccgag aacattggtt cctgtaggca tcgggattgg   6780
cggatcaaac actaaagcta ctggaacgag cagaagtcct ccggccgcca gttgccaggc   6840
ggtaaaggtg agcagaggca cgggaggttg ccacttgcgg gtcagcacgg ttccgaacgc   6900
catggaaacc gccccgcca  ggcccgctgc gacgccgaca ggatctagcg ctgcgtttgg   6960
tgtcaacacc aacagcgcca cgccgcagt  tccgcaaata gccccagga  ccgccatcaa   7020 tcgtatcggc ctacctagca gagcggcaga gatgaacacg accatcagcg gctgcacagc   7080
gcctaccgtc gccgcgaccc cgcccggcag gcggtagacc gaaataaaca acaagctcca   7140
gaatagcgaa atattaagtg cgccgaggat gaagatgcgc atccaccaga ttcccgttgg   7200
aatctgtcgg acgatcatca cgagcaataa acccgccggc aacgcccgca gcagcatacc   7260
```

-continued

```
ggcgacccct cggcctcgct gttcgggctc acgaaaacg ccggacagat gcgccttgtg    7320
agcgtccttg gggccgtcct cctgtttgaa gaccgacagc ccaatgatct cgccgtcgat    7380
gtaggcgccg aatgccacgg catctcgcaa ccgttcagcg aacgcctcca tgggcttttt    7440
ctcctcgtgc tcgtaaacgg acccgaacat ctctggagct ttcttcaggg ccgacaatcg    7500
gatctcgcgg aaatcctgca cgtcggccgc tccaagccgt cgaatctgag ccttaatcac    7560
aattgtcaat tttaatcctc tgtttatcgg cagttcgtag agcgcgccgt gcgtcccgag    7620
cgatactgag cgaagcaagt gcgtcgagca gtgcccgctt gttcctgaaa tgccagtaaa    7680
gcgctggctg ctgaaccccc agccggaact gaccccacaa ggccctagcg tttgcaatgc    7740
accaggtcat cattgaccca ggcgtgttcc accaggccgc tgcctcgcaa ctcttcgcag    7800
gcttcgccga cctgctcgcg ccacttcttc acgcgggtgg aatccgatcc gcacatgagg    7860
cggaaggttt ccagcttgag cgggtacggc tcccggtgcg agctgaaata gtcgaacatc    7920
cgtcgggccg tcggcgacag cttgcggtac ttctcccata tgaatttcgt gtagtggtcg    7980
ccagcaaaca gcacgacgat ttcctcgtcg atcaggacct ggcaacggga cgttttcttg    8040
ccacggtcca ggacgcggaa gcggtgcagc agcgacaccg attccaggtg cccaacgcgg    8100
tcggacgtga agcccatcgc cgtcgcctgt aggcgcgaca ggcattcctc ggccttcgtg    8160
taataccggc cattgatcga ccagcccagg tcctggcaaa gctcgtagaa cgtgaaggtg    8220
atcggctcgc cgataggggt gcgcttcgcg tactccaaca cctgctgcca caccagttcg    8280
tcatcgtcgg cccgcagctc gacgccggtg taggtgatct tcacgtcctt gttgacgtgg    8340
aaaatgacct tgttttgcag cgcctcgcgc gggattttct tgttgcgcgt ggtgaacagg    8400
gcagagcggg ccgtgtcgtt tggcatcgct cgcatcgtgt ccggccacgg cgcaatatcg    8460
aacaaggaaa gctgcatttc cttgatctgc tgcttcgtgt gtttcagcaa cgcggcctgc    8520
ttggcctcgc tgacctgttt tgccaggtcc tcgccggcgg ttttttcgctt cttggtcgtc    8580 atagttcctc gcgtgtcgat ggtcatcgac ttcgccaaac ctgccgcctc ctgttcgaga    8640
cgacgcgaac gctccacggc ggccgatggc gcgggcaggg caggggagc cagttgcacg    8700 ctgtcgcgct cgatcttggc cgtagcttgc tggaccatcg agccgacgga ctggaaggtt    8760
tcgcggggcg cacgcatgac ggtgcggctt gcgatggttt cggcatcctc ggcggaaaac    8820
cccgcgtcga tcagttcttg cctgtatgcc ttccggtcaa acgtccgatt cattcaccct    8880
ccttgcggga ttgccccgac tcacgccggg gcaatgtgcc cttattcctg atttgacccg    8940
cctggtgcct tggtgtccag ataatccacc ttatcggcaa tgaagtcggt cccgtagacc    9000
gtctggccgt ccttctcgta cttggtattc cgaatcttgc cctgcacgaa taccagcgac    9060
cccttgccca aatacttgcc gtgggcctcg gcctgagagc caaaacactt gatgcggaag    9120
aagtcggtgc gctcctgctt gtcgccggca tcgttgcgcc acatctaggt actaaaacaa    9180
ttcatccagt aaaatataat atttttatttt ctcccaatca ggcttgatcc ccagtaagtc    9240
aaaaaatagc tcgacatact gttcttcccc gatatcctcc ctgatcgacc ggacgcagaa    9300
ggcaatgtca taccacttgt ccgccctgcc gcttctccca agatcaataa agccacttac    9360
tttgccatct ttcacaaaga tgttgctgtc tcccaggtcg ccgtgggaaa agacaagttc    9420
ctcttcgggc ttttccgtct ttaaaaaatc atacagctcg cgcggatctt taaatggagt    9480
gtcttcttcc cagttttcgc aatccacatc ggccagatcg ttattcagta agtaatccaa    9540
ttcggctaag cggctgtcta agctattcgt atagggacaa tccgatatgt cgatggagtg    9600
```

```
aaagagcctg atgcactccg catacagctc gataatcttt tcagggcttt gttcatcttc    9660
atactcttcc gagcaaagga cgccatcggc ctcactcatg agcagattgc tccagccatc    9720
atgccgttca aagtgcagga cctttggaac aggcagcttt ccttccagcc atagcatcat    9780
gtccttttcc cgttccacat cataggtggt ccctttatac cggctgtccg tcattttaa     9840 atataggttt tcattttctc ccaccagctt atataccta gcaggagaca ttccttccgt     9900
atcttttacg cagcggtatt tttcgatcag ttttttcaat tccggtgata ttctcatttt    9960
agccatttat tatttccttc ctcttttcta cagtatttaa agataccca agaagctaat    10020 tataacaaga cgaactccaa ttcactgttc cttgcattct aaaaccttaa ataccagaaa   10080 acagctttt caaagttgtt ttcaaagttg gcgtataaca tagtatcgac ggagccgatt    10140
ttgaaaccac aattatgggt gatgctgcca acttactgat ttagtgtatg atggtgtttt   10200
tgaggtgctc cagtggcttc tgtgtctatc agctgtccct cctgttcagc tactgacggg   10260
gtggtgcgta acggcaaaag caccgccgga catcagcgct atctctgctc tcactgccgt   10320
aaaacatggc aactgcagtt cacttacacc gcttctcaac ccggtacgca ccagaaaatc   10380
attgatatgg ccatgaatgg cgttggatgc cgggcaacag cccgcattat gggcgttggc   10440
ctcaacacga ttttacgtca cttaaaaaac tcaggccgca gtcggtaacc tcgcgcatac   10500
agccgggcag tgacgtcatc gtctgcgcgg aaatggacga acagtggggc tatgtcgggg   10560
ctaaatcgcg ccagcgctgg ctgttttacg cgtatgacag tctccggaag acggttgttg   10620
cgcacgtatt cggtgaacgc actatggcga cgctggggcg tcttatgagc ctgctgtcac   10680
cctttgacgt ggtgatatgg atgacggatg gctggccgct gtatgaatcc cgcctgaagg   10740
gaaagctgca cgtaatcagc aagcgatata cgcagcgaat tgagcggcat aacctgaatc   10800
tgaggcagca cctggcacgg ctgggacgga agtcgctgtc gttctcaaaa tcggtggagc   10860
tgcatgacaa agtcatcggg cattatctga acataaaaca ctatcaataa gttggagtca   10920
ttacccaatt atgatagaat ttacaagcta taaggttatt gtcctgggtt tcaagcatta   10980
gtccatgcaa gttttatgc tttgcccatt ctatagatat attgataagc gcgctgccta   11040
tgccttgccc cctgaaatcc ttacatacgg cgatatcttc tatataaaag atatattatc   11100
ttatcagtat tgtcaatata ttcaaggcaa tctgcctcct catcctcttc atcctcttcg   11160
tcttggtagc ttttaaata tggcgcttca tagagtaatt ctgtaaaggt ccaattctcg   11220
ttttcatacc tcggtataat cttacctatc acctcaaatg gttcgctggg tttatcgcac   11280
ccccgaacac gagcacggca cccgcgacca ctatgccaag aatgcccaag gtaaaaattg   11340
ccggccccgc catgaagtcc gtgaatgccc cgacggccga agtgaagggc aggccgccac   11400
ccaggccgcc gccctcactg cccggcacct ggtcgctgaa tgtcgatgcc agcacctgcg   11460
gcacgtcaat gcttccgggc gtcgcgctcg ggctgatcgc ccatcccgtt actgccccga   11520
tcccggcaat ggcaaggact gccagcgctg ccattttttgg ggtgaggccg ttcgcggccg   11580
aggggcgcag cccctggggg gatgggaggc ccgcgttagc gggccgggag ggttcgagaa   11640 ggggggggcac cccccttcgg cgtgcgcggt cacgcgcaca gggcgcagcc ctggttaaaa   11700
acaaggttta taaatattgg tttaaaagca ggttaaaaga caggttagcg gtggccgaaa   11760
aacgggcgga aaccccttgca aatgctggat tttctgcctg tggacagccc ctcaaatgtc   11820
aataggtgcg cccctcatct gtcagcactc tgcccctcaa gtgtcaagga tcgcgcccct   11880
catctgtcag tagtcgcgcc cctcaagtgt caataccgca gggcacttat ccccaggctt   11940
gtccacatca tctgtgggaa actcgcgtaa aatcaggcgt tttcgccgat ttgcgaggct   12000
```

-continued

```
ggccagctcc  acgtcgccgg  ccgaaatcga  gcctgcccct  catctgtcaa  cgccgcgccg   12060
ggtgagtcgg  cccctcaagt  gtcaacgtcc  gcccctcatc  tgtcagtgag  ggccaagttt   12120
tccgcgaggt  atccacaacg  ccggcggccg  cggtgtctcg  cacacggctt  cgacggcgtt   12180
tctggcgcgt  ttgcagggcc  atagacggcc  gccagcccag  cggcgagggc  aaccagcccg   12240
g                                                                        12241
```

IDENTIFICATION AND CHARACTERIZATION OF AN ANTHOCYANIN MUTANT (*ANT1*) IN TOMATO

RELATED APPLICATIONS

This is a continuation-in-part of U.S. Ser. No. 10/033,190, filed Oct. 29, 2001. Priority is also claimed to U.S. provisional application Nos. 60/369,998 and 60/369,906, which were both filed on Apr. 4, 2002. The content of the prior applications is hereby incorporated by reference.

FIELD OF THE INVENTION

The present invention relates to a plant phenotype, designated Anthocyanin 1 (ANT1), together with DNA and polypeptide sequences associated with the same.

BACKGROUND OF THE INVENTION

Flavonoids comprise a diverse collection of red to blue colored secondary metabolites that accumulate in the tissues of many plant species. The primary structure of flavonoids consists of two aromatic carbon groups; benzopyran (A and C rings) and benzene (B ring). The variation in the heterocyclic C-ring of flavonoids and the interlinkage between the benzopyran and benzene groups are the basis for the classification of flavonoids into the flavone, flavonol, flavonone, isoflavone, anthocyanin, and flavane groups.

Anthocyanins have been associated with many important physiological and developmental functions in the plants, including, modification of the quantity and quality of captured light (Barker D H et al,. *Plant Cell and Environment* 20: 617-624, 1977.); protection from the effects of UV-B radiation (Burger J and Edwards G E. *Plant and Cell Physiology* 37: 395-399, 1996; Klaper R et al., *Photochemistry and Photobiology* 63: 811-813, 1996); defense against herbivores (Coley and Kusar. In: Mulkey S S, Chazdon R L, Smith A P, eds. Tropical Forest Plant Ecophysiology. New York: Chapman and Hall 305-335, 1996); and protection from photoinhibition (Gould K S, et al., Nature 378: 241-242, 1995; and Dodd I C et al,. *Journal of Experimental Botany* 49: 1437-1445, 1998); and scavenging of reactive oxygen intermediates in stressful environments (Furuta S et al., *Sweetpotato Res Front* (KNAES, Japan) 1:3, 1995; Sherwin H W and Farrant J M., *Plant Growth Regulation* 24: 203-210, 1998; and Yamasaki H *Trends in Plant Science* 2: 7-8, 1997).

Anthocyanins have demonstrated anti-oxidant activity, suggesting a role in protecting against cancer, cardiovascular and liver diseases (Kamei H et al., *J Clin Exp Med* 164: 829, 1993; Suda I, et al., 1997. *Sweetpotato Res Front (KNAES, Japan)* 4:3, 1997; and Wang C J, et al., H *Food Chem Toxicology* 38: 411-416, 2000). Thus, anthocyanin-rich foods and extracts have been studied for their utility in a variety of therapeutic applications (e.g. Katsube et al., J Agric Food Chem (2003) 51(1):68-75; Renaud et al., Lancet (1992) 339:1523-1526; and Natella et al., J Agric Food Chem (2002) 50(26):7720-7725). There is also interest in the use of anthocyanin-rich plant species in the production of natural dyes (Venturi and Piccaglia, "*The Rediscovery of Dye Plants as Promising "Non Food Crops"*", Interactive European Network for Industrial Crops and their Applications, Newsletter no. 10, November 1999).

Many steps in anthocyanin biosynthesis are shared among plant species, while the regulatory elements that underlie the expression level and pattern of genes encoding these enzymes are diverse. In *Petunia*, AN2 encodes a MYB domain protein that is orthologous to C1 from maize (Quattrocchio F et al., 1999, Plant Cell 11: 1433-1444), and *Arabidopsis* genes PAP1 and PAP2 (Borevitz et al., Plant Cell. 2000 December;12(12):2383-2394). The Anthocyanin1 gene (AN1) of petunia encodes a basic helix-loop-helix (bHLH) protein that activates the transcription of the structural anthocyanin gene Dihdroflavonol Reductates (DFR). The expression of AN1 is regulated by AN2 (Spelt et al., Plant Cell. 2000 September;12(9):1619-32). In *Arabidopsis*, two other transcription factors have been implicated in controlling the accumulation of flavonoids: the homeodomain protein Anthocyaninless2 (ANL2) is required for anthocyanin accumulation in subepidermal cells, while and the zinc finger protein, TT1, is involved in the accumulation of proanthocyanidin polymers in the seed coat (Kubo et al., Plant Cell. 1999 July;11(7):1217-26; Sagasser et al., Genes Dev. Jan. 1, 2002;16(1):138-49).

Isoflavones have also been widely studied for their potential therapeutic utility and health benefits (Hewitt and Singletary, Cancer Lett (2003) 192(2):133-143; Katz, J Altem Complement Med (2002) 8(6):813-821). Isoflavones play roles in plant pathogen response and in symbioses with rhizobial bacteria (Pueppke et al. 1998, Plant Physiol 117: 599-608). They occur almost exclusively in soybeans and other legumes (Jung et al. 2000, Nature Biotechnology 18:208-212). Three principle isoflavone aglycones occur in soybean: daidzein, genistein and glycitein. Glycitein accounts for only about 10% of the total isoflavone content (Song et al 1999, J Agric Food Chem 47:1607-1610), but some research suggests glycitein is both more bioavailable (Song et al 1999, J of Nutr. 129:957-962) and more estrogenic (Songe et al 1999, J Agric Food Chem, supra) than daidzein and genistein.

SUMMARY OF THE INVENTION

The invention provides nucleic acid and amino acid sequences associated with the Anthocyanin 1 ("ANT1") phenotype in plants, presented as modified leaf, flower or fruit color, and modified flavonoid production.

In one aspect, the invention provides one or more isolated ANT1 nucleic acid sequences comprising a nucleic acid sequence that encodes or is complementary to a sequence that encodes an ANT1 polypeptide having at least 70%, 80%, 90% or more sequence identity to the amino acid sequence presented as SEQ ID NO:2.

In another aspect, the polynucleotide comprises a nucleic acid sequence that hybridizes, under high, medium, or low stringency conditions to the nucleic acid sequence, or fragment thereof, presented as SEQ ID NO:1, or the complement thereof.

In a related aspect, expression of one or more of such ANT1 polynucleotides in a plant is associated with the ANT1 phenotype.

The invention further provides plant transformation vectors, plant cells, plant parts and plants comprising an ANT1 nucleic acid sequence.

Expression of such an ANT1 nucleic acid sequence in a plant is associated with the ANT1 phenotype, presented as a modified leaf, flower or fruit color phenotype.

The overexpression of ANT1 in a plant, and the ANT1 phenotype, is associated with increased production of specific anthocyanins. The invention provides transgenic tomato that over-expresses ANT1 and that produces anthocyanins selected from the group consisting of delphinidin 3-rutinoside-5-glucoside, delphinidin 3-(coumaroyl)rutinoside-5-glucoside, delphinidin 3-(caffeoyl)rutinoside-5-glucoside, petunidin 3-rutinoside-5-glucoside, petunidin 3-(coumaroyl)rutinoside-5-glucoside, petunidin 3-(caffeoyl)rutinoside-5-glucoside, malvidin3-rutinoside-5-glucoside, malvidin 3-(coumaroyl)rutinoside-5-glucoside, and malvidin 3-(caffeoyl)rutinoside-5-glucoside.

The invention further provides transgenic tobacco that over-expresses ANT1 and that produces cyanidin-3-glucoside and/or cyanidin-3-rutinoside.

The overexpression of ANT1 in a plant, and the ANT1 phenotype, is also associated with increased isoflavone production, particularly production of glycitein. In one specific embodiment, the invention provides transgenic tomato that over-expresses ANT1 and that produces glycitein.

In a further aspect the invention provides a method of modifying the ANT1 phenotype in a plant by introducing an ANT1 nucleic acid sequence into plant progenitor cells and growing the cells to produce a transgenic plant.

DETAILED DESCRIPTION OF THE INVENTION

Figure 1:
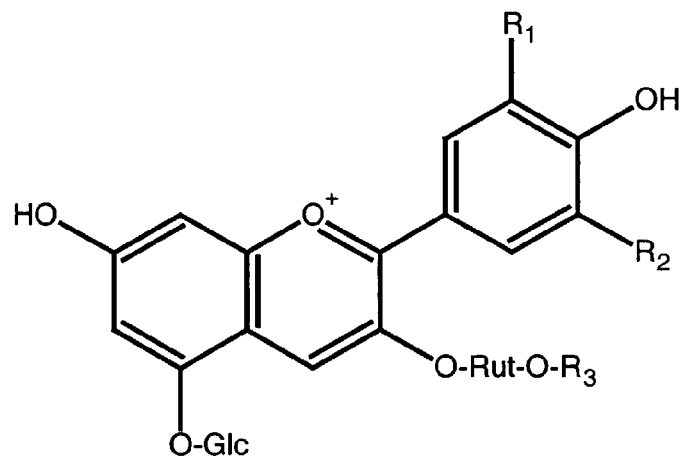
FIG. 1 presents the core chemical structure of the anthocyanins listed in Table 2 below.

I. Definitions.

Unless otherwise indicated, all technical and scientific terms used herein have the same meaning as they would to one skilled in the art of the present invention. Practitioners are particularly directed to Sambrook et al. Molecular Cloning: A Laboratory Manual (Second Edition), Cold Spring Harbor Press, Plainview, N.Y., 1989; and Ausubel F M et al. Current Protocols in Molecular Biology, John Wiley & Sons, New York, N.Y., 1993, for definitions and terms of the art.

All publications cited herein are expressly incorporated herein by reference for the purpose of describing and disclosing compositions and methodologies that might be used in connection with the invention. All cited patents, patent publications, and sequence and other information in referenced websites are also incorporated by reference.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence which is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1990) 215:403-410; blast.wustl.edu/blast/README.html website) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

The term "% homology" is used interchangeably herein with the term "% identity."

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, supra, Chapters 9 and 11, and in Ausubel, F. M., et al, supra). An example of high stringency conditions includes hybridization at about 42° C. in 50% formamide, 5×SSC, 5× Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a plant cell means the plant cell has a non-native (heterologous) nucleic acid sequence integrated into its genome which is maintained through two or more generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to a non-transgenic plant, as it is found in nature.

As used herein, the term "$T_1$" refers to the generation of plants from the seed of $T_0$ plants. The $T_1$ generation is the first set of transformed plants that can be selected by application of a selection agent, e.g., an antibiotic or herbicide, for which the transgenic plant contains the corresponding resistance gene.

As used herein, the term "$T_2$" refers to the generation of plants by self-fertilization of the flowers of $T_1$ plants, previously selected as being transgenic.

As used herein, the term "plant part" includes any plant organ or tissue including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic.

Thus a plant having within its cells a heterologous polynucleotide is referred to herein as a "transgenic plant". The heterologous polynucleotide can be either stably integrated into the genome, or can be extra-chromosomal. Preferably, the polynucleotide of the present invention is stably integrated into the genome such that the polynucleotide is passed on to successive generations. The polynucleotide is integrated into the genome alone or as part of a recombinant expression cassette. "Transgenic" is used herein to include any cell, cell line, callus, tissue, plant part or plant, the genotype of which has been altered by the presence of heterologous nucleic acids including those transgenics initially so altered as well as those created by sexual crosses or asexual reproduction of the initial transgenics.

A plant cell, tissue, organ, or plant into which the recombinant DNA constructs containing the expression constructs have been introduced is considered "transformed", "transfected", or "transgenic". A transgenic or transformed cell or plant also includes progeny of the cell or plant and progeny produced from a breeding program employing such a transgenic plant as a parent in a cross and exhibiting an altered phenotype resulting from the presence of a recombinant nucleic acid sequence. Hence, a plant of the invention will include any plant which has a cell containing a construct with introduced nucleic acid sequences, regardless of whether the sequence was introduced into the directly through transformation means or introduced by generational transfer from a progenitor cell which originally received the construct by direct transformation.

The terms "Anthocyanin 1" and "ANT1", as used herein encompass native Anthocyanin 1 (ANT1) nucleic acid and amino acid sequences, homologues, variants and fragments thereof.

An "isolated" ANT1 nucleic acid molecule is an ANT1 nucleic acid molecule that is identified and separated from at least one contaminant nucleic acid molecule with which it is ordinarily associated in the natural source of the ANT1 nucleic acid. An isolated ANT1 nucleic acid molecule is other than in the form or setting in which it is found in nature. However, an isolated ANT1 nucleic acid molecule includes ANT1 nucleic acid molecules contained in cells that ordinarily express ANT1 where, for example, the nucleic acid molecule is in a chromosomal location different from that of natural cells.

As used herein, the term "mutant" with reference to a polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

Generally, a "variant" polynucleotide sequence encodes a "variant" amino acid sequence which is altered by one or more amino acids from the reference polypeptide sequence. The variant polynucleotide sequence may encode a variant amino acid sequence having "conservative" or "non-conservative" substitutions. Variant polynucleotides may also encode variant amino acid sequences having amino acid insertions or deletions, or both.

As used herein, the term "phenotype" may be used interchangeably with the term "trait". The terms refer to a plant characteristic that is readily observable or measurable and results from the interaction of the genetic make-up of the plant with the environment in which it develops. Such a phenotype includes chemical changes in the plant make-up resulting from enhanced gene expression which may or may not result in morphological changes in the plant, but which are measurable using analytical techniques known to those of skill in the art.

II. The Identified ANT1 Phenotype and Gene.

The gene and phenotype of this invention were identified in a screen using activation tagging. Activation tagging is a process by which a heterologous nucleic acid construct comprising a nucleic acid control sequence, e.g. an enhancer, is inserted into a plant genome. The enhancer sequences act to enhance transcription of one or more native plant genes (Walden et. al., EMBO J. 13: 4729-36, 1994; Walden et al., *Plant Mol. Biol.* 26: 1521-8, 1994; and Weigel D, et al., *Plant Physiology,* 122:1003-1013, 2000).

Briefly, a large number of tomato (*Lycopersium esculentum*) cv. Micro-Tom plants were transformed with a modified form of the activation tagging vector pSKI015 (Weigel et al, supra), which comprises a T-DNA (i.e., the sequence derived from the Ti plasmid of *Agrobacterium tumifaciens* that are transferred to a plant cell host during *Agrobacterium* infection), an enhancer element and a selectable marker gene. The construct, pAG3202, is further described in the Examples. Following random insertion of pAG3202 into the genome of transformed plants, the enhancer element can result in up-regulation genes in the vicinity of the T-DNA insertion, generally within 5-10 kilobase (kb) of the insertion. In the $T_1$ generation, plants were exposed to the selective agent in order to specifically recover those plants that expressed the selectable marker and therefore harbored insertions of the activation-tagging vector. Transformed plants were observed for interesting phenotypes, which are generally identified at the $T_1$, $T_2$ and/or $T_3$ generations. Genomic sequence surrounding the T-DNA insertion is analyzed in order to identify genes responsible for the interesting phenotypes. Genes responsible for causing such phenotypes are identified as attractive targets for manipulation for agriculture, food, ornamental plant, and/or pharmaceutical industries.

The present invention provides a modified leaf, flower or fruit color phenotype, identified in ACTTAG Mico-Tom lines that were observed at the callus stage as having purple color and purple shoots. Purple plants were derived from purple colored caulogenic callus in culture. The clonal plant lines (i.e., additional shoots originating from the same purple colored caulogenic callus or those multiplied from the first purple plant either in tissue culture or by cuttings in the greenhouse) were identified as having purple coloration on leaves, sepals and flowers. The plants were also observed to exhibit a modified fruit color described as a deeper red color relative to wild type Micro-Tom plants. The phenotype and associated gene have been designated Anthocyanin 1 ("ANT1").

The invention also provides a newly identified and isolated nucleic acid sequence that was identified by analysis of the genomic DNA sequence surrounding the T-DNA insertion correlating with the ANT1 phenotype. In particular, applicants have identified and characterized the open reading frame of the ANT1 gene, which is specifically overexpressed in plants having the ANT1 phenotype, and which is provided in SEQ ID NO:1. A detailed description of the isolation and characterization of ANT1 is set forth in the Examples.

III. Compositions of the Invention

A. ANT1 Nucleic Acids

The ANT1 gene may be used in the development of transgenic plants having a desired phenotype. This may be accomplished using the native ANT1 sequence, a variant ANT1 sequence or a homologue or fragment thereof.

An ANT1 nucleic acid sequence of this invention may be a DNA or RNA sequence, derived from genomic DNA, cDNA or mRNA. The nucleic acid sequence may be cloned, for example, by isolating genomic DNA from an appropriate source, and amplifying and cloning the sequence of interest using PCR. Alternatively, nucleic acid sequence may be synthesized, either completely or in part, especially where it is desirable to provide plant-preferred sequences. Thus, all or a portion of the desired structural gene (that portion of the gene which encodes a polypeptide or protein) may be synthesized using codons preferred by a selected host.

The invention provides a polynucleotide comprising a nucleic acid sequence which encodes or is complementary to a sequence which encodes an ANT1 polypeptide having the amino acid sequence presented in SEQ ID NO:2 and a polynucleotide sequence identical over its entire length to the ANT1 nucleic acid sequence presented SEQ ID NO:1. The invention also provides the coding sequence for the mature ANT1 polypeptide, a variant or fragment thereof, as well as the coding sequence for the mature polypeptide or a fragment thereof in a reading frame with other coding sequences, such as those encoding a leader or secretory sequence, a pre-, pro-, or prepro-protein sequence.

An ANT1 polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

When an isolated polynucleotide of the invention comprises an ANT1 nucleic acid sequence flanked by non-ANT1 nucleic acid sequence, the total length of the combined polynucleotide is typically less than 25 kb, and usually less than 20 kb, or 15 kb, and in some cases less than 10 kb, or 5 kb.

In addition to the ANT1 nucleic acid and corresponding polypeptide sequences described herein, ANT1 variants can be prepared by introducing appropriate nucleotide changes into the ANT1 nucleic acid sequence; by synthesis of the desired ANT1 polypeptide or by altering the expression level of the ANT1 gene in plants. For example, amino acid changes may alter post-translational processing of the ANT1 polypeptide, such as changing the number or position of glycosylation sites or altering the membrane anchoring characteristics.

In one aspect, preferred ANT1 coding sequences include a polynucleotide comprising a nucleic acid sequence which encodes or is complementary to a sequence which encodes an ANT1 polypeptide having at least 50%, 60%, 70%, 75%, 80%, 85%, 90%, 95% or more sequence identity to the amino acid sequence presented in SEQ ID NO:2.

In another aspect, preferred variants include an ANT1 polynucleotide sequence that is at least 50% to 60% identical over its entire length to the ANT1 nucleic acid sequence presented as SEQ ID NO:1, and nucleic acid sequences that are complementary to such an ANT1 sequence. More preferable are ANT1 polynucleotide sequences comprise a region having at least 70%, 80%, 85%, 90% or 95% or more sequence identity to the ANT1 sequence presented as SEQ ID NO:1.

In a related aspect, preferred variants include polynucleotides that are be "selectively hybridizable" to the ANT1 polynucleotide sequence presented as SEQ ID NO:1.

Sequence variants also include nucleic acid molecules that encode the same polypeptide as encoded by the ANT1 polynucleotide sequence described herein. Thus, where the coding frame of an identified nucleic acid molecule is known, for example by homology to known genes or by extension of the sequence, a number of coding sequences can be produced as a result of the degeneracy of the genetic code. For example, the triplet CGT encodes the amino acid arginine. Arginine is alternatively encoded by CGA, CGC, CGG, AGA, and AGG. Such substitutions in the coding region fall within the sequence variants that are covered by the present invention. Any and all of these sequence variants can be utilized in the same way as described herein for the identified ANT1 parent sequence, SEQ ID NO:1.

Such sequence variants may or may not selectively hybridize to the parent sequence. This would be possible, for example, when the sequence variant includes a different codon for each of the amino acids encoded by the parent nucleotide. In accordance with the present invention, also encompassed are sequences that are at least 70% identical to such degeneracy-derived sequence variants.

Although ANT1 nucleotide sequence variants are preferably capable of hybridizing to the nucleotide sequences recited herein under conditions of moderately high or high stringency, there are, in some situations, advantages to using variants based on the degeneracy of the code, as described above. For example, codons may be selected to increase the rate at which expression of the peptide occurs in a particular prokaryotic or eukaryotic organism, in accordance with the optimum codon usage dictated by the particular host organism. Alternatively, it may be desirable to produce RNA having longer half lives than the mRNA produced by the recited sequences.

Variations in the native full-length ANT1 nucleic acid sequence described herein, may be made, for example, using any of the techniques and guidelines for conservative and non-conservative mutations, as generally known in the art, oligonucleotide-mediated (site-directed) mutagenesis, alanine scanning, and PCR mutagenesis. Site-directed mutagenesis (Kunkel T A et al., *Methods Enzymol.* 204:125-39, 1991); cassette mutagenesis (Crameri A and Stemmer W P, *Bio Techniques* 18(2):194-6, 1995.); restriction selection mutagenesis (Haught C et al. *BioTechniques* 16(1):47-48, 1994), or other known techniques can be performed on the cloned DNA to produce nucleic acid sequences encoding ANT1 variants.

In addition, the gene sequences associated the ANT1 phenotype may be synthesized, either completely or in part, especially where it is desirable to provide host-preferred sequences. Thus, all or a portion of the desired structural gene (that portion of the gene which encodes the protein) may be synthesized using codons preferred by a selected host. Host-preferred codons may be determined, for example, from the codons used most frequently in the proteins expressed in a desired host species.

It is preferred that an ANT1 polynucleotide encodes an ANT1 polypeptide that retains substantially the same biological function or activity as the mature ANT1 polypeptide encoded by the polynucleotide set forth as SEQ ID NO:1 (i.e. results in an ANT1 phenotype when overexpressed in a plant).

Variants also include fragments of the ANT1 polynucleotide of the invention, which can be used to synthesize a full-length ANT1 polynucleotide. Preferred embodiments include polynucleotides encoding polypeptide variants wherein 5 to 10, 1 to 5, 1 to 3, 2, 1 or no amino acid residues of an ANT1 polypeptide sequence of the invention are substituted, added or deleted, in any combination. Particularly preferred are substitutions, additions, and deletions that are silent such that they do not alter the properties or activities of the polynucleotide or polypeptide.

A nucleotide sequence encoding an ANT1 polypeptide can also be used to construct hybridization probes for further genetic analysis. Screening of a cDNA or genomic library with the selected probe may be conducted using standard procedures, such as described in Sambrook et al., supra). Hybridization conditions, including moderate stringency and high stringency, are provided in Sambrook et al., supra.

The probes or portions thereof may also be employed in PCR techniques to generate a pool of sequences for identification of closely related ANT1 sequences. When ANT1 sequences are intended for use as probes, a particular portion of an ANT1 encoding sequence, for example a highly conserved portion of the coding sequence may be used.

For example, an ANT1 nucleotide sequence may be used as a hybridization probe for a cDNA library to isolate genes, for example, those encoding naturally-occurring variants of ANT1 from other plant species, which have a desired level of sequence identity to the ANT1 nucleotide sequence disclosed in SEQ ID NO:1. Exemplary probes have a length of about 20 to about 50 bases.

In another exemplary approach, a nucleic acid encoding an ANT1 polypeptide may be obtained by screening selected cDNA or genomic libraries using the deduced amino acid sequence disclosed herein, and, if necessary, using conventional primer extension procedures as described in Sambrook et al., supra, to detect ANT1 precursors and processing intermediates of mRNA that may not have been reverse-transcribed into cDNA.

As discussed above, nucleic acid sequences of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like.

Once the desired form of an ANT1 nucleic acid sequence, homologue, variant or fragment thereof, is obtained, it may be modified in a variety of ways. Where the sequence involves non-coding flanking regions, the flanking regions may be subjected to resection, mutagenesis, etc. Thus, transitions, transversions, deletions, and insertions may be performed on the naturally occurring sequence.

With or without such modification, the desired form of the ANT1 nucleic acid sequence, homologue, variant or fragment thereof, may be incorporated into a plant expression vector for transformation of plant cells.

B. ANT1 Polypeptides

In one preferred embodiment, the invention provides an ANT1 polypeptide, having a native mature or full-length ANT1 polypeptide sequence comprising the sequence presented in SEQ ID NO:2. An ANT1 polypeptide of the invention can be the mature ANT1 polypeptide, part of a fusion protein or a fragment or variant of the ANT1 polypeptide sequence presented in SEQ ID NO:2.

Ordinarily, an ANT1 polypeptide of the invention has at least 50% to 60% identity to an ANT1 amino acid sequence over its entire length. More preferable are ANT1 polypeptide sequences that comprise a region having at least 70%, 80%, 85%, 90% or 95% or more sequence identity to the ANT1 polypeptide sequence of SEQ ID NO:2.

Fragments and variants of the ANT1 polypeptide sequence of SEQ ID NO:2, are also considered to be a part of the invention. A fragment is a variant polypeptide that has an amino acid sequence that is entirely the same as part but not all of the amino acid sequence of the previously described polypeptides. Exemplary fragments comprises at least 10, 20, 30, 40, 50, 75, or 100 contiguous amino acids of SEQ ID NO:2. The fragments can be "free-standing" or comprised within a larger polypeptide of which the fragment forms a part or a region, most preferably as a single continuous region. Preferred fragments are biologically active fragments, which are those fragments that mediate activities of the polypeptides of the invention, including those with similar activity or improved activity or with a decreased activity. Also included are those fragments that antigenic or immunogenic in an animal, particularly a human.

ANT1 polypeptides of the invention also include polypeptides that vary from the ANT1 polypeptide sequence of SEQ ID NO:2. These variants may be substitutional, insertional or deletional variants. The variants typically exhibit the same qualitative biological activity as the naturally occurring analogue, although variants can also be selected which have modified characteristics as further described below.

A "substitution" results from the replacement of one or more nucleotides or amino acids by different nucleotides or amino acids, respectively.

An "insertion" or "addition" is that change in a nucleotide or amino acid sequence which has resulted in the addition of one or more nucleotides or amino acid residues, respectively, as compared to the naturally occurring sequence.

A "deletion" is defined as a change in either nucleotide or amino acid sequence in which one or more nucleotides or amino acid residues, respectively, are absent.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances.

Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids.

Substitutions are generally made in accordance with known "conservative substitutions". A "conservative substitution" refers to the substitution of an amino acid in one class by an amino acid in the same class, where a class is defined by common physicochemical amino acid side chain properties and high substitution frequencies in homologous proteins found in nature (as determined, e.g., by a standard Dayhoff frequency exchange matrix or BLOSUM matrix). (See generally, Doolittle, R. F., OF URFS and ORFS (University Science Books, Calif., 1986).)

A "non-conservative substitution" refers to the substitution of an amino acid in one class with an amino acid from another class.

ANT1 polypeptide variants typically exhibit the same qualitative biological activity as the naturally occurring analogue, although variants also are selected to modify the characteristics of the ANT1 polypeptide, as needed. For example, glycosylation sites, and more particularly one or more O-linked or N-linked glycosylation sites may be altered or removed. For example, amino acid changes may alter post-translational processes of the ANT1 polypeptide, such as changing the number or position of glycosylation sites or altering the membrane anchoring characteristics.

The variations can be made using methods known in the art such as oligonucleotide-mediated (site-directed) mutagenesis, alanine scanning, and PCR mutagenesis. Site-directed mutagenesis (Carter et al., *Nucl. Acids Res.* 13:4331, 1986; Zoller et al., *Nucl. Acids Res.* 10:6487, 1987), cassette mutagenesis (Wells et al., *Gene* 34:315, 1985), restriction selection mutagenesis (Wells et al., *Philos. Trans. R. Soc.* London SerA 317:415, 1986) or other known techniques can be performed on the cloned DNA to produce the ANT1 polypeptide-encoding variant DNA.

Also included within the definition of ANT1 polypeptides are other related ANT1 polypeptides. Thus, probe or degenerate PCR primer sequences may be used to find other related polypeptides. Useful probe or primer sequences may be designed to all or part of the ANT1 polypeptide sequence, or to sequences outside the coding region. As is generally known in the art, preferred PCR primers are from about 15 to about 35 nucleotides in length, with from about 20 to about 30 being preferred, and may contain inosine as needed. The conditions for the PCR reaction are generally known in the art.

Covalent modifications of ANT1 polypeptides are also included within the scope of this invention. For example, the invention provides ANT1 polypeptides that are a mature protein and may comprise additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. Cellular enzymes can be used to remove any additional amino acids from the mature protein (Creighton, T. E., PROTEINS: STRUCTURE AND MOLECULAR PROPERTIES, W. H. Freeman & Co., San Francisco, pp. 79-86, 1983).

In a preferred embodiment, overexpression of an ANT1 polypeptide or variant thereof is associated with the ANT1 phenotype.

C. Antibodies.

The present invention further provides anti-ANT1 polypeptide antibodies. The antibodies may be polyclonal, monoclonal, humanized, bispecific or heteroconjugate antibodies.

Polyclonal antibodies can be produced in a mammal, for example, following one or more injections of an immunizing agent, and preferably, an adjuvant. Typically, the immunizing agent and/or adjuvant will be injected into the mammal by a series of subcutaneous or intraperitoneal injections. The immunizing agent may include an ANT1 polypeptide or a fusion protein thereof. It may be useful to conjugate the antigen to a protein known to be immunogenic in the mammal being immunized.

Alternatively, the anti-ANT1 polypeptide antibodies may be monoclonal antibodies. Monoclonal antibodies may be produced by hybridomas, wherein a mouse, hamster, or other appropriate host animal, is immunized with an immunizing agent to elicit lymphocytes that produce or are capable of producing antibodies that will specifically bind to the immunizing agent (Kohler and Milstein, *Nature* 256: 495, 1975). Monoclonal antibodies may also be made by recombinant DNA methods, such as those described in U.S. Pat. No. 4,816,567.

The anti-ANT1 polypeptide antibodies of the invention may further comprise humanized antibodies or human antibodies. The term "humanized antibody" refers to humanized forms of non-human (e.g., murine) antibodies that are chimeric antibodies, immunoglobulin chains or fragments thereof (such as Fv, Fab, Fab', F(ab')$_2$ or other antigen-binding partial sequences of antibodies) which contain some portion of the sequence derived from non-human antibody. Methods for humanizing non-human antibodies are well known in the art, as further detailed in Jones et al., *Nature* 321:522-525, 1986; Riechmann et al., *Nature* 332:323-327, 1988; and Verhoeyen et al., *Science* 239:1534-1536, 1988. Methods for producing human antibodies are also known in the art. (Jakobovits, A, et al., Ann N Y Acad Sci 764:525-35, 1995; Jakobovits, A, Curr Opin Biotechnol, 6(5):561-6, 1995.

In one exemplary approach, anti-ANT1 polyclonal antibodies are used for gene isolation. Western blot analysis may be conducted to determine that ANT1 or a related protein is present in a crude extract of a particular plant species. When reactivity is observed, genes encoding the related protein may be isolated by screening expression libraries representing the particular plant species. Expression libraries can be constructed in a variety of commercially available vectors, including lambda gt11, as described in Sambrook, et al., supra.

IV. Utility of the ANT1 Phenotype and Gene

From the foregoing, it can be appreciated that the ANT1 nucleotide sequence, protein sequence and phenotype find utility in modulated expression of the ANT1 protein and the development of non-native phenotypes associated with such modulated expression.

The ANT1 phenotype has features that distinguish the mutant from wild type plants, including modified leaf color, modified flower color and modified fruit color. We have shown that the modified pigmentation phenotype is associated with increased production of specific anthocyanins, which vary according to individual plant species.

In one aspect, the modified leaf, flower and fruit color of plants having the ANT1 phenotype finds utility in the development of improved ornamental plants, fruits and/or cut flowers.

In another aspect, the modified anthocyanin content in plants having the ANT1 phenotype finds utility in plant-derived food, food additives, nutrition supplements, and natural dyes.

The ANT1 gene may be used to generate transgenic plants that produce flavonoids including anthocyanins and isoflavones. When separation from other plant material is desired, flavonoids may be extracted by any method known in the art (Yang et al., J Chromatogr A (2001) 928(2):163-170; Di Mauro et al., J. Agric. Food Chem (2002) 50:5968-5974; Matsumoto et al., J. Agric. Food Chem (2001) 49:1541-1545). An extracted flavonoid may be substantially purified or may be used in an unprocessed or partially processed state.

In one preferred embodiment, the invention provides transgenic tomato that produces at least one anthocyanin selected from delphinidin 3-rutinoside-5-glucoside, delphinidin 3-(coumaroyl)rutinoside-5-glucoside, delphinidin 3-(caffeoyl)rutinoside-5-glucoside, petunidin 3-rutinoside-5-glucoside, petunidin 3-(coumaroyl)rutinoside-5-glucoside, petunidin 3-(caffeoyl)rutinoside-5-glucoside, malvidin3-rutinoside-5-glucoside, malvidin 3-(coumaroyl) rutinoside-5-glucoside, and malvidin 3-(caffeoyl)rutinoside-5-glucoside. In a further preferred embodiment, the anthocyanin is produced at a level that is at least 5-, 10-, 20-, 50-, or 100-fold that observed in the non-transgenic plant.

In another preferred embodiment, the invention provides transgenic tobacco that produces at least one anthocyanin selected from cyanidin-3-glucoside and cyanidin-3-rutinoside. In a further preferred embodiment, the anthocyanin is produced at a level that is at least 5-, 10-, 20-, 50-, or 100-fold that observed in the non-transgenic plant.

We have further found that over-expression of the ANT1 gene in tomato results in isoflavone production, which is otherwise undetectable. Accordingly, ANT1 genes can be used in the generation of transgenic soy or other legumes with altered isoflavone content or composition. ANT1 genes can also be used to produce isoflavones in plants other than legumes. In one embodiment, plants are generated that have increased glycitein content. In another embodiment, the isoflavone is produced at a level of at least 1.00 mg/100 g. Thus, the ANT1 gene may be used to generate transgenic plants that produce desired metabolites, including isoflavones. The isoflavones may be extracted by any method known in the art.

In another aspect, as further described in the Examples, the ANT1 gene has utility as a transformation marker in genetically manipulated plants.

In practicing the invention, the ANT1 phenotype and modified ANT1 expression is generally applicable to any type of plant, as further detailed below.

The methods described herein are generally applicable to all plants. Although activation tagging and gene identification was carried out in tomato, following identification of a nucleic acid sequence and associated phenotype, the selected gene, a homologue, variant or fragment thereof, may be expressed in any type of plant. In one aspect, the invention is directed to fruit- and vegetable-bearing plants.

The invention is generally applicable to plants which produce fleshy fruits; for example but not limited to, tomato (*Lycopersicum*); grape (*Vitas*); ); strawberry (*Fragaria*); raspberry, blackberry, loganberry (*Rubus*); currants and gooseberry (*Ribes*); blueberry, bilberry, whortleberry, cranberry (*Vaccinium*); kiwifruit and Chinese gooseberry (*Actinida*); apple (*Malus*); pear (*Pyrus*); melons (*Cucumis* sp.) members of the *Prunus* genera, e.g. plum, chery, nectarine and peach; sapota (*Manilkara zapotilla*); mango; avocado; apricot; peaches; cherries; pineapple; papaya; passion fruit; citrus; date palm; banana; plantain; and fig.

Similarly, the invention is applicable to vegetable plants, including, but not limited to sugar beets, green beans, broccoli, brussel sprouts, cabbage, celery, chard, cucumbers, eggplants, peppers, pumpkins, rhubarb, winter squash, summer squash, zucchini, lettuce, radish, carrot, pea, potato, corn, murraya and herbs.

In a related aspect, the invention is directed to the cut flower industry, grain-producing plants, oil-producing plants and nut-producing plants, as well as other crops including, but not limited to, cotton (*Gossypium*), alfalfa (*Medicago sativa*), flax (*Linum usitatissimum*), tobacco (*Nicotiana*), turfgrass (Poaceae family), and other forage crops. Suitable transformation techniques for these and other plants are known in the art.

A wide variety of transformation techniques exist in the art, and new techniques are continually becoming available.

Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to Agrobacterium-mediated transformation, electroporation, microinjection, microprojectile bombardment calcium-phosphate-DNA co-precipitation or liposome-mediated transformation of a heterologous nucleic acid construct comprising the ANT1 coding sequence. The transformation of the plant is preferably permanent, i.e. by integration of the introduced expression constructs into the host plant genome, so that the introduced constructs are passed onto successive plant generations.

In one embodiment, binary Ti-based vector systems may be used to transfer and confirm the association between enhanced expression of an identified gene with a particular plant trait or phenotype. Standard Agrobacterium binary vectors are known to those of skill in the art and many are commercially available, such as pBI121 (Clontech Laboratories, Palo Alto, Calif.).

The optimal procedure for transformation of plants with Agrobacterium vectors will vary with the type of plant being transformed. Exemplary methods for Agrobacterium-mediated transformation include transformation of explants of hypocotyl, shoot tip, stem or leaf tissue, derived from sterile seedlings and/or plantlets. Such transformed plants may be reproduced sexually, or by cell or tissue culture. Agrobacterium transformation has been previously described for a large number of different types of plants and methods for such transformation may be found in the scientific literature.

Depending upon the intended use, a heterologous nucleic acid construct may be made which comprises a nucleic acid sequence associated with the ANT1 phenotype, and which encodes the entire protein, or a biologically active portion thereof for transformation of plant cells and generation of transgenic plants.

The expression of an ANT1 nucleic acid sequence or a homologue, variant or fragment thereof may be carried out under the control of a constitutive, inducible or regulatable promoter. In some cases expression of the ANT1 nucleic acid sequence or homologue, variant or fragment thereof may regulated in a developmental stage or tissue-associated or tissue-specific manner. Accordingly, expression of the nucleic acid coding sequences described herein may be regulated with respect to the level of expression, the tissue type(s) where expression takes place and/or developmental stage of expression leading to a wide spectrum of applications wherein the expression of an ANT1 coding sequence is modulated in a plant.

Strong promoters with enhancers may result in a high level of expression. When a low level of basal activity is desired, a weak promoter may be a better choice. Expression of ANT1 nucleic acid sequence or homologue, variant or fragment thereof may also be controlled at the level of transcription, by the use of cell type specific promoters or promoter elements in the plant expression vector.

Numerous promoters useful for heterologous gene expression are available. Exemplary constitutive promoters include the raspberry E4 promoter (U.S. Pat. Nos. 5,783,393 and 5,783,394), the 35S CaMV (Jones J D et al, Transgenic Res 1:285-297 1992), the CsVMV promoter (Verdaguer B et al., Plant Mol Biol 37:1055-1067, 1998) and the melon actin promoter. Exemplary tissue-specific promoters include the tomato E4 and E8 promoters (U.S. Pat. No. 5,859,330) and the tomato 2AII gene promoter (Van Haaren M J J et al., Plant Mol Bio 21:625-640, 1993).

When ANT1 sequences are intended for use as probes, a particular portion of an ANT1 encoding sequence, for example a highly conserved portion of a coding sequence may be used.

In yet another aspect, in some cases it may be desirable to inhibit the expression of endogenous ANT1 sequences in a host cell. Exemplary methods for practicing this aspect of the invention include, but are not limited to antisense suppression (Smith, et al., *Nature* 334:724-726, 1988); co-suppression (Napoli, et al, *Plant Cell* 2:279-289, 1990); ribozymes (PCT Publication WO 97/10328); and combinations of sense and antisense (Waterhouse, et al., *Proc. Natl. Acad. Sci. USA* 95:13959-13964, 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. In some cases, it may be desirable to inhibit expression of the ANT1 nucleotide sequence. This may be accomplished using procedures generally employed by those of skill in the art together with the ANT1 nucleotide sequence provided herein.

Standard molecular and genetic tests may be performed to analyze the association between a cloned gene and an observed phenotype. A number of other techniques that are useful for determining (predicting or confirming) the function of a gene or gene product in plants are described below.

1. DNA/RNA Analysis

DNA taken form a mutant plant may be sequenced to identify the mutation at the nucleotide level. The mutant phenotype may be rescued by overexpressing the wild type (WT) gene. The stage- and tissue-specific gene expression patterns in mutant vs. WT lines, for instance, by in situ hybridization, may be determined. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing (Baulcombe D, *Arch Virol Suppl* 15:189-201, 1999).

In a preferred application, microarray analysis, also known as expression profiling or transcript profiling, is used to simultaneously measure differences or induced changes in the expression of many different genes. Techniques for microarray analysis are well known in the art (Schena M et al., Science (1995) 270:467-470; Baldwin D et al., *Cur Opin Plant Biol.* 2(2):96-103, 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Microarray analysis of individual tagged lines may be carried out, especially those from which genes have been isolated. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical or signaling pathway based on its overexpression phenotype or by sequence homology with related genes. Alternatively, analysis may comprise genetic crosses with WT lines and other mutant lines (creating double mutants) to order the gene in a pathway, or determining the effect of a mutation on expression of downstream "reporter" genes in a pathway.

4. Other Analyses

Other analyses may be performed to determine or confirm the participation of the isolated gene and its product in a particular metabolic or signaling pathway, and to help determine gene function.

Generation of Mutated Plants with an ANT1 Phenotype

The invention further provides a method of identifying plants that have mutations in, or an allele of, endogenous ANT1 that confer an ANT1 phenotype, and generating progeny of these plants that also have the ANT1 phenotype and are not genetically modified. In one method, called "TILLING" (for Targeting Induced Local Lesions IN Genomes), mutations are induced in the seed of a plant of interest, for example, using EMS treatment. The resulting plants are grown and self-fertilized, and the progeny are used to prepare DNA samples. ANT1-specific PCR is used to identify whether a mutated plant has an ANT1 mutation. Plants having ANT1 mutations may then be tested for the ANT1 phenotype, or alternatively, plants may be tested for the ANT1 phenotype, and then ANT1-specific PCR is used to determine whether a plant having the ANT1 phenotype has a mutated ANT1 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene/Quantitative Trait Locus (QTLs) approach can be used in a marker-assisted breeding program to identify alleles of or mutations in the ANT1 gene or orthologs of ANT1 that may confer the ANT1 phenotype (see Foolad et al., Theor Appl Genet. (2002) 104(6-7):945-958; Rothan et al., Theor Appl Genet (2002) 105(1): 145-159) Dekkers and Hospital, Nat Rev Genet. (2002) Jan;3(1):22-32).

Thus, in a further aspect of the invention, an ANT1 nucleic acid is used to identify whether a plant having an ANT1 phenotype has a mutation in endogenous ANT1 or has a particular allele that causes the ANT1 phenotype compared to plants lacking the mutation or allele, and generating progeny of the identified plant that have inherited the ANT1 mutation or allele and have the ANT1 phenotype. The ANT1 plants generated can be used as non-genetically modified foods having increased flavonoid content, and can also be used for the same purposes described herein for transgenic ANT1 plants (e.g. extraction of natural dyes, etc.).

EXAMPLE 1

Generation of Plants with an ANT1 Phenotype by Transformation with an Activation Tagging Construct A. *Agrobacterium* Vector Preparation.

Mutants were generated using a modified version of the activation tagging "ACTTAG" vector, pSKI015 (GenBank Identifier [GI] 6537289; Weigel D et al., supra). This binary vector, called pAG3202, contains the following components: the pSKI backbone; a 4×35S enhancer consisting of four tandem repeats of the enhancer region from the CaMV 35S promoter including 4 Alu1-EcoRV fragments in tandem, 129 bp of CaMV sequence associated with each tandem Alu1-EcoRV repeat, and an additional 7 bp repeated sequence that is not in the 35S enhancer region of the native CaMV genome; the nptII selectable marker under the control of a raspberry E4 (RE4) promoter; an *Agrobacterium* gene 7 termination element located downstream of the nptII gene, adjacent the left border of the plasmid.

Single colonies of *Agrobacterium tumefaciens* strains EHA 105/EHA 101/GV3101 containing the binary plasmid pAG3202 were grown in MGL medium at pH 5.4 overnight and diluted to approximately $5\times10^8$ cells/ml with MGL or liquid plant co-cultivation medium.

For long-term storage, PCR-positive colonies were grown in selective media, glycerol added to a final concentration of 30% and cultures quick frozen, then stored at −80° C. For the initiation of dense *Agrobacterium* cultures for plant transformation, stock cultures were grown in selective media, glycerol added to a final concentration of 30%, and a number of 20 µl aliquots quick frozen in liquid nitrogen and stored at −80° C.

B. Transformation and Selection of Micro-Tom Mutants

Seeds of (*Lycopersium esculentum*) were surface sterilized in 25% bleach with tween-20 for 15 minutes and rinsed with sterile water before plating on seed germination medium (MS salts, Nitsch vitamins, 3% sucrose and 0.7% agar, pH 5.8), modified by the addition of auxin and/or cytokinins and giberrellic acid as necessary. The cultures were incubated at 24° C. with a 16 hr photo period (50-60 $\mu mol.m^{-2}s^{-1}$). Seven to ten day old seedlings and one month old in vitro plants were used for hypocotyl explants.

Hypocotyls were cut into 3-5 mm segments, then immersed in bacterial suspension, blotted on sterile filter paper and placed on co-cultivation medium. The explants were immersed in bacterial suspension, blotted on sterile filter paper and placed on co-cultivation medium (MS salts, LS vitamins, 3% sucrose, 0.1 mg/l kinetin, 0.2 mg/l 2,4-D, 200 mg/l potassium acid phosphate, 50 µM acetosyringone and 0.7% agar, pH 5.4) for 2-3 days.

After two to three days of co-culture, the explants were transferred to shoot regeneration medium containing MS salts, Nitsch vitamins, 3% sucrose, 2 mg/l zeatin, 500 mg/l carbenicillin, 200 mg/L timetin and 0.7% agar at pH 5.8, supplemented with the antibiotic, kanamycin at 75-400 mg/l in order to select for nptII-expressing transformants. The selection level of antibiotic was gradually raised over an 8-week period based on the tissue response.

The explants were transferred to fresh medium every two weeks. Initiation of callus with signs of shoot initials was observed from 3-6 weeks depending on the type of explant. Callusing and shoot regeneration was observed to continue over approximately 4 months after which the explant tissues decline. A purple callus was observed among the tissue growing on the selection medium. Regenerated shoots displayed a variety of color phenotypes and were entirely green, entirely purple, or mix of green and purple to various degrees. Green shoots of approximately 1 cm in size with distinct shoot meristems were excised from the callus and transferred to root induction medium containing MS salts, Nitsch vitamins, 3% sucrose, 1 mg/l IBA, 50 mg/l kanamycin, 100 mg/l carbenicillin or 100 mg/L timetin and 0.7% agar, pH 5.8. The rooted plants were out-planted to soil in a Biosafety greenhouse.

Plants were transported to greenhouse facilities, potted up in 3.5" pots tagged for plant identification.

Transformants were observed at the callus stage and after $T_1$ plants were established in the greenhouse for phenotypic variations relative to wild-type Micro-Tom plants. To achieve this, several wild-type plants were kept in close proximity to the transgenic plants. Each plant was observed closely twice a week with observations noted and documented by photographs.

Images of each pool of 8 plants were recorded using a Digital camera (DC-260), and morphology observations were made at about four weeks after planting.

Eleven Micro-Tom lines were developed from the callus originally identified by its purple color and purple shoots at the caulogenic stage. The clonal plant lines were identified as having modified leaf color with a heavy purple cast on leaves, modified flower color characterized by purple striations on petals and sepals and flowers with a purple cast mixed with the normal yellow color of the corolla. The plants were also observed to exhibit a modified fruit color described as a deeper red color relative to wild type Micro-Tom plants. The clonal plant lines (mutants) were designated Anthocyanin1 ("ANT1").

The ANT1 mutant was identified from fewer than 2000 individual Micro-Tom tomato ACTTAG lines that were developed following tissue culture transformation with the binary plasmid pAG3202, and selection on kanamycin-containing medium.

Observations were made and photos taken of the clonal $T_1$ ANT1 plant lines that exhibited the ANT1 phenotype, designated H000001484, H000001624, H000001708, H000001709, H000001710, H000001711, H000001712, H000001713, H000001715, H000001716 and H000001717.

Seeds were collected from $T_1$ plants from line H000001624 and grown to generate $T_2$ plants. From the 11 out of the 18 seeds that germinated, and 8 plants displayed purple coloration, confirming that ANT1 is a dominant, gain of function mutation, following typical Mendelian segregation.

The results indicated that ANT1 is a gain of function trait, expected from activation tagging based over-expression of a native gene.

EXAMPLE 2

Characterization of Plants That Exhibit the ANT1 Phenotype.

Micro-Tom genomic DNA was extracted from the H000001484 clone of the activation tagged mutant originally identified at the callus stage, in sufficient yield and quality for plasmid rescue of activation tagged plant lines using the procedure described below. Further analysis was performed using combined tissue derived from the H000001624, H000001708, H000001709, H000001710, H000001711, H000001712, H000001713, H000001715, H000001716 and H000001717 plant lines.

A. Micro-Tom Tomato Genomic DNA Extraction

Nucleon™ PhytoPure™ systems (Plant and fungal DNA extraction kits) from Amersham™ were used for extracting genomic DNA. Methods were essentially as follows:

1.0 g of fresh tissue from the H000001484 clone was ground in liquid nitrogen to yield a free flowing powder, then transferred to a 15 ml polypropylene centrifuge tube. 4.6 ml of Reagent 1 from the Nucleon Phytopure kit was added with thorough mixing, followed by addition of 1.5 ml of Reagent 2 from the Nucleon Phytopure kit, with inversion until a homogeneous mixture was obtained. The mixture was incubated at 65° C. in a shaking water bath for 10 minutes, and placed on ice for 20 minutes. The samples were removed from the ice, 2 ml of −20° C. chloroform added, mixed and centrifuged at 1300 g for 10 minutes. The supernatant was transferred into a fresh tube, 2 ml cold chloroform, 200 µl of Nucleon PhytoPure DNA extraction resin suspension added and the mixture shaken on a tilt shaker for 10 minutes at room temperature, then centrifuged at 1300 g for 10 minutes. Without disturbing the Nucleon resin suspension layer, the upper DNA-containing phase was transferred into a fresh tube, centrifuged at 9500 rpm for 30 minutes to clarify the transferred aqueous phase if the upper phase appeared cloudy, an equal volume of cold isopropanol added, and the tube gently inverted until DNA precipitated. It was then pelleted by centrifugation, washed with cold 70% ethanol, pelleted again, and air-dried.

DNA was resuspended in TE buffer (10 mM Tris. HCl, pH 7.4, 1 mM EDTA), containing RNase, incubated at 55° C. for 15 minutes, further extracted phenol/chloroform, then chloroform, run on a 1% agarose gel to check the DNA Quality, the DNA concentration determined by a DNA fluorometer (Hoeffer DyNA Quant 200).

DNA extracted from shoots of the H000001484 ANT1 clone at the caulogenic callus stage and from wild type plants was PCR-amplified using primers that amplify a 35S enhancer sequence, and primers that amplify a region of the pBluescript vector sequence in pAG3202. Amplification using primers that span the 35S enhancer region resulted in a ladder of products, indicating that all four copies of the 35S enhancer were present. Amplification using primers to the pBluescript vector was done primarily to detect the T-DNA insert(s) in transformed plants and has been optimized for the following conditions: annealing temp: 57° C., 30 cycles [94° C., 30 sec; 57° C., 1 min; 72° C., 1 min] 1 cycle [72° C., 7 min].

The ACTTAG™ line, H000001484 (ANT1), was confirmed as positive for the presence of 35S enhancer and pAG3202 vector sequences by PCR, and as positive for Southern hybridization verifying genomic integration of the ACTTAG DNA and showing the presence of a single T-DNA insertion in the clonal transgenic line.

B. Plasmid Rescue

Genomic DNA from the H000001484 clonal line was digested by the restriction enzymes used in Southern Hybridization. The restriction fragments were self-ligated and used to transform the *E. coli* cells. The plasmids that contained a full-length pBluescript vector, 4×35S enhancer, and a right border T-DNA flanking genomic DNA fragment were rescued.

More specifically, genomic DNA was digested with Hind III and Xho I under standard reaction conditions at 37° C. overnight.

The ligation reactions were set up containing the following and left at 16° C. overnight:

| | |
|---|---|
| Digested Genomic DNA | 40 µl |
| 5X Ligation Buffer | 50 µl |
| Ligase (Gibcol, 1 U/µl) | 10 µl |
| ddH$_2$O | 150 µl |

The ligated DNA precipitated, resuspended in ddH$_2$O and used to transform *E. coli* SURE cells (Stratagene) via electroporation, with 10 pg of pUC18 plasmid as a control.

The transformation mixture was spread on two LB-plates containing 100 µg/ml ampicillin and incubated overnight at 37° C. Single colonies were picked from the plates and used to start a 5 ml LB-ampicillin broth culture from each colony by culturing overnight at 37° C. The plasmid was extracted from the culture and restriction digested to confirm the size of genomic insertion.

C. Sequencing Of Rescued Plasmids

Sequencing was accomplished using a ABI Prism Big-Dye™ Terminator Cycle Sequencing Ready Reaction Kit (PE Applied Biosystem), AmpliTaq DNA Polymerase (Perkin-Elmer), an ABI Prism™ 310 Genetic Analyzer (Perkin-Elmer) and sequence analysis software, e.g., Sequencer™ 3.1.1 or MacVector 6.5.3. Sequencing was done essentially according to manufacturers' protocols The left ends of plasmids rescued were sequenced across the right T-DNA border.

The rescued sequence was subjected to analysis using the BLAST sequence comparison programs at the www.ncbi.nlm.nih.gov/BLAST website. A basic BLASTN search identified a sequence with 31% identity to the Anthocyanin 2 (An2) mRNA of *Petunia integrifolia* (GI 7673087 and 7673085). The presence of an open reading frame (i.e., the ANT1 cDNA) was predicted using the BLASTX program.

RT-PCR analysis confirmed that the gene whose nucleotide sequence is presented as SEQ ID NO:1 (ANT1) was specifically overexpressed in tissue from plants having the ANT1 phenotype. Specifically, RNA was extracted from combined tissues derived from the H000001624 clonal plant line, which exhibited the ANT1 phenotype, and from wild type plants. RT-PCR was performed using primers specific to the sequence presented as SEQ ID NO:1 and a constitutively expressed actin gene (positive control). The results showed that plants displaying the ANT1 phenotype overexpressed the mRNA for the ANT1 gene, indicating the enhanced expression of the ANT1 gene correlated with the ANT1 phenotype.

The amino acid sequence predicted from the ANT1 nucleic acid sequence was determined using Vector NTI (InforMax, North Bethesda, Md.) and is presented in SEQ ID NO:2. A Basic BLASTP 2.0.11 search using the ncbi.nlm.nih.gov/BLAST website and the predicted ANT1 amino acid sequence was conducted. Results indicated that the predicted ANT1 protein sequence has 49% identitiy to the *Petunia integrifolia* An2 protein sequence (GI 7673088 and 7673086) and 65%-85% identity to several Myb-related transcription factors in the N-terminal region, from approximately aa 1-120 of SEQ ID NO:2. These Myb-related proteins included An2 from *Petunia×hybrida* (GI 7673084), the *Zea mays* C1-I (GI 22214), the *Zea mays* PL transcription factor (GI 2343273) and an *Arabidopsis* transcription factor (GI 3941508). The *Petunia* An2 gene is a regulator of the Anthocyanin biosynthetic pathway (Quattrocchio et al, supra).

These results suggest that ANT1 is associated with modified leaf, flower or fruit color in Micro-tomato.

EXAMPLE 3

Confirmation of Phenotype/Genotype Association in Micro-Tomato

In order to further confirm the association between the ANT1 phenotype and the ANT1 gene presented in SEQ ID NO: 1, a genomic fragment comprising the ANT1 gene, provided in SEQ ID NO:3, was over-expressed in wild type Micro-Tom plants. Specifically, this 1012 bp genomic fragment, including the ANT1 coding regions, was cloned into the multiple cloning site (MCS) of the binary vector pAG2370. pAG2370, whose sequence is provided in SEQ ID NO:4, comprises the vector backbone from the binary vector pBIN19 (GI1256363), T-DNA left and right border fragments, and, between border fragments, the CsVMV promoter sequence and a Nos termination sequence for controlling expression of the inserted gene, and the neomycin phosphotransferase (NPTII) gene, which confers kanamycin resistance, whose expression is controlled by the RE4 promoter (U.S. Pat. No. 6,054,635) and the G7 termination sequence. The ANT1 fragment was cloned into SmaI/SpeI sites of pAG2370, inserted between the CsVMV promoter region, proximal to the 5' end of genomic fragment, and the Nos termination sequence, proximal to the 3' end of the genomic fragment. The pAG2370-ANT1 construct was transformed into *Agrobacterium tumefaciens* by electroporation.

The pAG2370-ANT1 construct described above was introduced into wild-type Micro-Tom plants via *Agrobacterium*-mediated transformation, essentially as described in Example 1. Briefly, explants were dissected from Micro-Tom seedlings. Explants were inoculated by soaking in the *Agrobacterium* suspension for 15 to 120 minutes, blotted on sterile filter paper to remove excess bacteria, and plated. Explants were co-cultivated in non-selective media for 2-4 days at 24° C. with a 16-hour photoperiod, after which they were transferred to selective media (with kanamycin) and returned to the growth room. Explants were transferred to fresh medium every two weeks until shoots were 0.5 to 1 cm tall. Shoots were excised from the explants, placed on selective medium with kanamycin in Phytatrays (Sigma), and returned to the growth room for two to four weeks. Shoots were observed for rooting, and rooted shoots were out-planted to soil and acclimated to the greenhouse. The transformation process generated 64 independent $T_0$ events. Morphological observations demonstrated that 45 transgenic plants displayed the ANT1 purple color phenotype and were either partially or entirely purple. Tissue was collected from six $T_1$ plants showing the ANT1 phenotype, and RT-PCR was carried out using wild type as a control. While no ANT1 gene expression could be detected in the wild-type control, five out of the six plants displaying the ANT1 phenotype over-expressed the ANT1 transcript. The internal control experiments, using a constitutively expressed actingene, showed that all samples had similar levels of the actin expression.

EXAMPLE 4

Confirmation of Phenotype/Genotype Association in *Arabidopsis*

In order to further confirm the association between the ANT1 phenotype and the ANT1 gene in plants other than Micro-Tom, the ANT1 gene was introduced into and over-expressed in wild type *Arabidopsis thaliana*.

The pAG2370-ANT1 construct described above was introduced into wild-type *Arabidopsis* plants via *Agrobacterium*-mediated transformation using standard vacuum infiltration methods. All infiltrated seeds were plated in selective media containing kanamycin, and kanamycin-resistant $T_1$ plants were transplanted to 72-cell flats. The transformation process generated 10 independent $T_0$ events, of which seven displayed the ANT1 purple coloration phenotype in at least part of the plant. Tissue was collected from four $T_1$ plants showing the ANT1 phenotype, and RT-PCR was carried out using wild type as a control. While no ANT1 gene expression could be detected in the wild-type control, all plants displaying the ANT1 phenotype over-expressed the ANT1 transcript. The internal control experiments, using a constitutively expressed actin gene, showed that all samples had similar levels of the actin expression.

EXAMPLE 5

Confirmation of Phenotype/Genotype Association in Tobacco

In order to further confirm the association between the ANT1 phenotype and the ANT1 gene in plants other than Micro-Tom, the ANT1 gene was introduced into and overexpressed in wild type *Nicotiana tabacum* (tobacco, Wisconsin-38 type).

The pAG2370-ANT1 construct described above was introduced into wild-type tobacco plants via *Agrobacterium*-mediated transformation using essentially the following methods. In order to generate tobacco plants for transformation, tobacco seeds were germinated as follows: seeds were shaken about ten minutes on a lab shaker, in a solution containing approximately 1.3% to 2.1% sodium hypochlorite and one drop of Tween-20 (Polyoxyethylenesorbitan monolaurate) per 100 milliliters. Seeds were then washed in sterile water and sterilely transferred to the surface of TbSG medium (4.3 g/l Murashige and Skoog salts, Phytotech; 1 ml/l MS vitamins, Sigma; 30 g/l sucrose; 8 g/l agar, Sigma; pH adjusted to ~5.8) in petri dishes or Phytatrays (Sigma), 10-50 seeds per vessel, and incubated in light at 25° C. Tobacco plants were dissected on sterile filter paper moistened with sterile, deionized water or liquid TbCo medium (4.3 g/l Murashige and Skoog salts, Phytotech; 1 ml/l MS vitamins, Sigma; 30 g/l sucrose; 200 mg/l $KH_2PO_4$; 2 mg/l Indole-3-acetic acid; 0.25 mg/l Kinetin; 0 to 100 µM Acetosyringone; 7 g/l Agar, Sigma; pH adjusted to 5.4-5.6). Explants with cut edges on all sides could be generated by cutting the leaf from the plant, dissecting out and discarding the midvein, and cutting the leaf lamina into 3 to 5 mm squares. Alternatively, discs could be cut from the lamina using a sterilized cork borer.

Explants were inoculated by soaking for 15-120 minutes in *Agrobacterium* suspension ($OD_{600}$ between 0.175 and 0.225) prepared with the pAG2370-ANT1 construct, then blotted and plated on TbCo medium. Explants were co-cultivated 2-4 days at 24° C. with a 16-hour photoperiod, and then transferred to Tb selective medium (4.3 g/l Murashige and Skoog salts; 1 ml/l Nitsch and Nitsch vitamins, Duchefa; 30 g/l sucrose; 0.5 to 2 mg/l 6-Benzylaminopurine; 0 to 1 mg/l Naphthylacetic Acid; 0 to 750 mg/l Carbenicillin; 0 to 300 mg/l Timentin; 0 to 500 mg/l Kanamycin; 7 to 8 g/l Agar, Sigma; pH adjusted to ~5.8) containing kanamycin and re-transferred every two weeks until shoots were 0.5 to 1 cm tall. Shoots were excised from the explants, placed on TbR medium (4.3 g/l Murashige and Skoog salts; 1 ml/l Nitsch and Nitsch vitamins, Duchefa; 30 g/l sucrose; 0 to 1 mg/l Indole-3-butyric acid; 0 to 1 mg/l Naphthylacetic Acid; 0 to 100 mg/l Carbenicillin; 0 to 200 mg/l Timentin; 0 to 100 mg/l Kanamycin; 7 to 8 g/l Agar, Sigma; pH adjusted to ~5.8.) with kanamycin in Phytatrays, and grown two to four weeks, after which time the rooted shoots were planted to soil.

The transformation process generated 89 independent $T_0$ events, of which 54 displayed the ANT1 purple coloration phenotype in at least part of the plant. Tissue was collected from five $T_1$ plants showing the ANT1 phenotype, and RT-PCR was carried out using wild type as a control. While no ANT1 gene expression could be detected in the wild-type control, all plants displaying the ANT1 phenotype overexpressed the ANT1 transcript. The internal control experiments, using a constitutively expressed actin gene, showed that all samples had similar levels of the actin expression.

EXAMPLE 6

Use of the ANT1 Gene as a Transformation Marker in Tomato and Tobacco

Having successfully recapitulated the ANT1 phenotype in tomato and tobacco, as described above, we tested the utility of the ANT1 gene for utility as a transformation marker, based on its characteristic purple color, in these species. We transformed tobacco and Micro-Tom explants with the pAG2370-ANT1 vector, using methods described in the above Examples, grew the explants in the presence and absence of antibiotic (kanamycin), and compared transformation frequency based on rooting in the presence of antibiotic in the media to transformation frequency based on purple color. Results are shown in the Table below.

TABLE 1

Transformation frequency of tobacco and tomato, based on antibiotic selection or color

| Species | Kanamycin in media | # explants | Transformation frequency based on rooting in presence of antibiotic | Transformation frequency based on purple color |
|---|---|---|---|---|
| Tobacco | | | | |
| Wisconsin | + | 82 | 126%* | 80% |
| | − | 60 | — | 45% |
| Tomato | | | | |
| Micro-Tom | + | 103 | 77% | 54% |
| | − | 52 | — | 6% |

*This number reflects multiple transgenic events per original explant. When callus initiation occurs at two or three distinct points on the original explant, each is dissected and tested for shoot regeneration.

The results indicated that the ANT1 gene could be successfully used for screening of positive transformants in cultures of tomato and tobacco, and may be useful in other plants as well.

EXAMPLE 7

Anthocyanin Analysis in Tomato and Tobacco Over-Expressing ANT1

We performed liquid chromatography/mass spectrometry (LC/MS) analysis to characterize the anthocyanins produced in transgenic tomato and tobacco that mis-express ANT1.

Fresh tissue samples included leaves from wild-type micro-tom plants, from the original ACTTAG mutant line H000001624 ("ANT1 micro-tom"), and from plants in which pAG2370-ANT1 had been introduced ("recapitulated" ANT1 micro-tom), as well as tobacco leaves from plants in which pAG2370-ANT1 had been introduced ("ANT1 tobacco"). Frozen tissue samples included leaves from ANT1 micro-tom and from recapitulated ANT1 micro-tom, and a pool of in vitro shoots of ANT1 tomato.

To obtain tissue extracts, fresh or frozen plant material (0.5 g) was soaked for 2 hrs in 1 ml of either 1% HCl/MeOH or 5% HOAc(aq). The extracted plant material was separated from the liquid phase by filtration or centrifugation and the extract was transferred to 2 ml vials for HPLC analysis.

The crude plant extract (10 ul) was injected onto a Waters 2795 HPLC equipped with a Waters C-18, 3.5 um SymmetryShield column (4.6×150 mm). The extracts were eluted with a 30 minute mobile phase gradient of 5-35% ACN in 1.5% H3PO4(aq) with a flow rate of 1 ml/min. Compounds were detected at 520 nm using a Waters 996 photodiode array detector.

For LC/MS analysis, extracts (5 ul) were chromatographed on a C-18 Symmetry column with a 0.1% formic acid(aq)/ACN mobile phase running at 0.3 ml/min. A Micromass Quattro Micro triple quadrupole mass spectrometer with an ES+ source was used to detect and analyze all components of the extract.

We compared the anthocyanin composition in the leaves of several ANT1, recapitulated ANT1, and wild-type micro-tom. All of the ANT1 micro-tom plants were found to contain a similar mixture of at least nine different anthocyanins, although the ratios of the components varied. These anthocyanins appear to be elevated more than 100-fold compared to the wild-type (where they are almost undetectable), although concentrations differed from plant to plant, with the highest levels occurring in recapitulated lines. Mass spectral fragmentation of the nine anthocyanin molecular ions yielded one of three daughter ions at 303, 317, or 331 atomic mass units (AMU), indicating the presence of delphinidin, petunidin, and malvidin-type anthocyanidins (aglycones), respectively. With knowledge of the core structures, we realized that each anthocyanidin must be functionalized in the same three ways. Comparison of the molecular weights and MS fragmentation patterns of the tomato anthocyanins with common anthocyanin glycosylation motifs indicated that the ANT1 tomato produces the anthocyanins listed in Table 2 below, and depicted in FIG. 1. Anthocyanins designated (*) in Table 2 have been reported in light stressed tomatoes (Bory et al, The Plant Cell (2002) 14:2509-2526). Presence of the remaining six molecules in tomato has not been reported previously.

TABLE 2

| Substitution Pattern (FIG. 1) | Anthocyanin | Molecular Ion (M+) |
|---|---|---|
| $R_1$ = OH, $R_2$ = OH, $R_3$ = H | Delphinidin 3-rutinoside-5-glucoside | 773.4 |
| $R_1$ = OH, $R_2$ = OH, $R_3$ = Coumarate | Delphinidin 3-(coumaroyl)rutinoside-5-glucoside | 919.6 |
| $R_1$ = OH, $R_2$ = OH, $R_3$ = Caffeate | Delphinidin 3-(caffeoyl)rutinoside-5-glucoside | 935.6 |
| $R_1$ = OMe, $R_2$ = OH, $R_3$ = H | Petunidin 3-rutinoside-5-glucoside | 787.4 |
| $R_1$ = OMe, $R_2$ = OH, $R_3$ = Coumarate | Petunidin 3-(coumaroyl)rutinoside-5-glucoside (*) | 933.6 |
| $R_1$ = OMe, $R_2$ = OH, $R_3$ = Caffeate | Petunidin 3-(caffeoyl)rutinoside-5-glucoside (*) | 949.6 |
| $R_1$ = OMe, $R_2$ = OMe, $R_3$ = H | Malvidin 3-rutinoside-5-glucoside | 801.4 |
| $R_1$ = OMe, $R_2$ = OMe, $R_3$ = Coumarate | Malvidin 3-(coumaroyl)rutinoside-5-glucoside (*) | 947.6 |
| $R_1$ = OMe, $R_2$ = OMe, $R_3$ = Caffeate | Malvidin 3-(caffeoyl)rutinoside-5-glucoside | 963.6 |

Figure 2A:
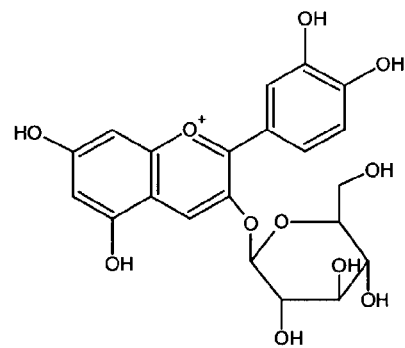
FIGS. 2a and 2b present the predicted chemical structures of the anthocyanins isolated from tobacco that over-expresses the ANT1 gene, specifically cyanidin-3-glucoside (FIG. 2a) and cyanidin-3-rutinoside (FIG. 2b).
Figure 2B:
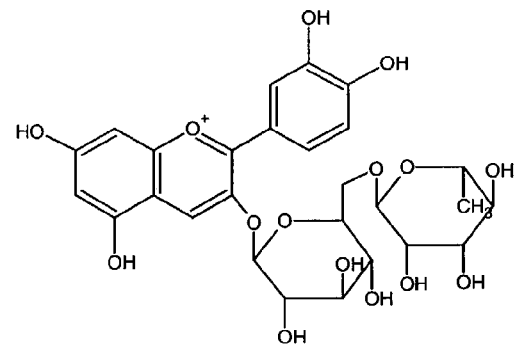

LC/MS analysis of ANT1 tobacco indicated two major anthocyanins with molecular weights of 449 and 595. Both components fragmented to give daughter ions at 287 amu, indicating a cyanidin type nucleus. Since cyanidins commonly occur as glycosides, we deduced that ANT1 tobacco contains mainly cyanidin-3-glucoside and cyanidin-3-rutinoside (FIG. 2).

EXAMPLE 8

Isoflavone Analysis in Tomato Over-expressing ANT1

Because isoflavones are derived from the phenylpropanoid pathway that also gives rise to anthocyanins, we analyzed fruits and leaves from an ANT1 and wild type micro-tomato for daidzein, genistein, and glycitein.

Isoflavone analysis was performed by Covance Laboratories Inc (Madison Wis.) according to the method of Seo and Morr (1984, J Agric Food Chem 32: 530-533) and Petterson and Kiessling (1984, J Assoc Off Anal Chem, 67:503-506). The detection limit of the analysis was 1.0 mg/100 g for glycitein, daidzein and genistein. As expected, wild type tomato had no detectable isoflavones in either leaves or fruit. However, leaves of ANT1 micro-tomato produced detectable levels of glycitein at nearly twice the detection limit. Leaves of ANT1 produced glycitein at 1.91 mg/100 g compared to <1.00 mg/100 g in the wild type.

It is claimed:

1. A transgenic plant, comprising a plant transformation vector comprising a nucleic acid sequence which encodes an ANT1 polypeptide having the amino acid sequence of SEQ ID NO: 2, wherein the plant has an ANT1 phenotype.

2. The transgenic plant of claim 1, wherein the plant is tomato or tobacco.

3. The transgenic plant of claim 2, wherein the transgenic plant is tomato, and wherein the tomato produces an anthocyanin selected from the group consisting of delphinidin 3-rutinoside-5-glucoside, delphinidin 3-(coumaroyl)rutinoside-5-glucoside, delphinidin 3-(caffeoyl)rutinoside-5-glucoside, petunidin 3-rutinoside-5-glucoside, petunidin 3-(coumaroyl)rutinoside-5-glucoside, petunidin 3-(caffeoyl)rutinoside-5-glucoside, malvidin3-rutinoside-5-glucoside, malvidin 3-(coumaroyl)rutinoside-5-glucoside, and malvidin 3-(caffeoyl)rutinoside-5-glucoside.

4. The transgenic plant of claim 2, wherein the plant is tobacco, and wherein the tobacco produces an anthocyanin selected from the group consisting of cyaniding-3-glucoside and cyaniding-3-rutinoside.

5. A method of isolating an anthocyanin from a plant, said method comprising introducing into progenitor cells of the plant a plant transformation vector comprising a nucleic acid sequence which encodes an ANT1 polypeptide having at least 95% sequence identity to the amino acid sequence SEQ ID NO: 2, growing the transformed progenitor cells to produce a transgenic plant having an ANT1 phenotype that expresses the polynucleotide sequence comprised by the vector, and extracting the anthocyanin from the plant.

6. The plant of claim 5, wherein the plant is tomato or tobacco.

7. The method of claim 5, wherein the anthocyanin is selected from the group consisting of delphinidin 3-rutinoside-5-glucoside, delphinidin 3-(coumaroyl)rutinoside-5-glucoside, deiphinidin 3-(caffeoyl)rutinoside-5-glucoside, petunidin 3-(coumaroyl)rutinoside-5-glucoside, malvidin3-rutinoside-5-glucoside, and malvidin 3(caffeoyl)rutinoside-5-glucoside.

8. The method of claim 5, wherein the nucleic acid sequence encodes an ANT1 polypeptide having the amino acid sequence of SEQ ID NO: 2.

9. A method of isolating glycetein from a plant, said method comprising introducing into progenitor cells of the plant a plant transformation vector comprising a nucleic acid sequence which encodes an ANT1 polypeptide having at least 95% sequence identity to the amino acid sequence SEQ ID NO: 2, growing the transformed progenitor cells to produce a transgenic plant having an ANT1 phenotype that expresses the polynucleotide sequence comprised by the vector, and extracting the glycetein from the plant.

10. The method of claim 9, wherein the plant is tomato.

11. The method of claim 9, wherein the nucleic acid sequence encodes an ANT1 polypeptide having the amino acid sequence of SEQ ID NO: 2.

* * * * *

UNITED STATES PATENT AND TRADEMARK OFFICE
CERTIFICATE OF CORRECTION

PATENT NO. : 7,304,207 B2  Page 1 of 1
APPLICATION NO. : 10/407845
DATED : December 4, 2007
INVENTOR(S) : Connors et al.

It is certified that error appears in the above-identified patent and that said Letters Patent is hereby corrected as shown below:

In Claim 3 (Col. 41, line 28), "malvidin3-rutinoside-5-glucoside" should read --malvidin 3-rutinoside-5-glucoside--.

In Claim 4 (Col. 41, line 33), "cyaniding-3-glucoside" should read --cyanidin-3-glucoside--.

In Claim 4 (Col. 41, line 34), "cyaniding-3-rutinoside" should read --cyanidin-3-rutinoside--.

In Claim 7 (Col. 42, line 19), "deiphinidin 3-(caffeoyl)rutinoside-5-glucoside" should read --delphinidin 3-(caffeoyl)rutinoside-5-glucoside--.

In Claim 7 (Col. 42, line 20), "malvidin3-rutinoside-5-glucoside" should read --malvidin 3-rutinoside-5-glucoside--.

In Claim 7 (Col. 42, line 22), "malvidin 3(caffeoyl)rutinoside-5-glucoside" should read --malvidin 3-(caffeoyl)rutinoside-5-glucoside--.

In Claim 9 (Col. 42, line 28), "glycetein" should read --glycitein--.

In Claim 9 (Col. 42, line 36), "glycetein" should read --glycitein--.

Signed and Sealed this

Second Day of June, 2009

JOHN DOLL
*Acting Director of the United States Patent and Trademark Office*